(12) United States Patent
Zhang et al.

(10) Patent No.: US 10,132,811 B2
(45) Date of Patent: Nov. 20, 2018

(54) SALIVARY TRANSCRIPTOMIC AND MICROBIAL BIOMARKERS FOR PANCREATIC CANCER

(75) Inventors: Lei Zhang, Los Angeles, CA (US); David T. Wong, Beverly Hills, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 288 days.

(21) Appl. No.: 13/379,341

(22) PCT Filed: Jun. 25, 2010

(86) PCT No.: PCT/US2010/040025
§ 371 (c)(1),
(2), (4) Date: Mar. 16, 2012

(87) PCT Pub. No.: WO2010/151789
PCT Pub. Date: Dec. 29, 2010

(65) Prior Publication Data
US 2012/0196764 A1    Aug. 2, 2012

Related U.S. Application Data

(60) Provisional application No. 61/220,482, filed on Jun. 25, 2009.

(51) Int. Cl.
*C12Q 1/68*      (2018.01)
*G01N 33/574*    (2006.01)
*C12Q 1/6886*    (2018.01)

(52) U.S. Cl.
CPC ..... *G01N 33/57488* (2013.01); *C12Q 1/6886* (2013.01); *G01N 33/57438* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2005/0106642 A1 | 5/2005 | Lipps et al. | |
| 2006/0257903 A1* | 11/2006 | Akil et al. | 435/6 |
| 2007/0203083 A1* | 8/2007 | Mootha et al. | 514/44 |
| 2008/0075722 A1* | 3/2008 | DePinho et al. | 424/138.1 |
| 2008/0131887 A1* | 6/2008 | Stephan et al. | 435/6 |
| 2008/0242742 A1* | 10/2008 | Depinho | A01K 67/0276 514/789 |
| 2008/0280772 A1* | 11/2008 | Wong et al. | 506/9 |
| 2009/0099789 A1* | 4/2009 | Stephan et al. | 702/20 |
| 2009/0175827 A1* | 7/2009 | Byrom et al. | 424/93.2 |
| 2009/0192111 A1* | 7/2009 | Bader et al. | 514/44 |
| 2009/0258002 A1* | 10/2009 | Barrett et al. | 424/130.1 |
| 2010/0160177 A1* | 6/2010 | Merbl et al. | 506/9 |
| 2011/0009469 A1* | 1/2011 | Mendell | A61K 31/145 514/44 A |
| 2011/0320392 A1* | 12/2011 | Black et al. | 706/21 |

OTHER PUBLICATIONS

Author Unknown. "GeneChip Human Genome Arrays—The Most Comprehensive Coverage of All Well-Substantiated Genes in the Human Genome". *Affimetrix Data Sheet*. (2004).
Conrads et al., "Testing for Marker Bacteria in Progressive Periodontitis: The European Experience". *Infectious Diseases in Clinical Practice*. vol. 10, pp. 481-487. (2001).
Gu et al., "Bacterial 16S rRNA/rDNA Profiling in the Liquid Phase of Human Saliva". *The Open Dentistry Journal*. vol. 3, pp. 80-84. (2009).
Mulcahy et al., "A Prospective Study of K-ras Mutations in the Plasma of Pancreatic Cancer Patients". *Clinical Cancer Research*. vol. 4, pp. 271-275. (1998).
Wong et al., "Salivary biomarkers for pancreatic cancer detection". *Journal of Clinical Oncology*. vol. 27, No. 15S, Abstract. (2009).
Zhang et al., "Multiple Salivary Biomarkers for Pancreatic Cancer Detection". *International Association for Dental Research General Session and Exhibition*. Abstract. (2009).
Zhang et al., "Salivary Transcriptomic Biomarkers for Detection of Resectable Pancreatic Cancer." *Gastroenterology*. vol. 138, No. 3. (2010).
Anon. 'GeneChip® Human Genome Arrays' Affymetrix Data Sheet [retrieved on Jun. 30, 2014]. Retrieved from Internet <http://media.affymetrix.com/support/technical/datasheets/human_datasheet.pdf> copyright 2003-2004.

* cited by examiner

*Primary Examiner* — Catherine S Hibbert
(74) *Attorney, Agent, or Firm* — Riverside Law LLP

(57) ABSTRACT

The present invention relates to the identification of pancreatic cancer biomarkers for the detection of early pancreatic cancer. The present invention also provides methods of diagnosing pancreatic cancer and distinguishing between pancreatic cancer and chronic pancreatitis. The present invention additionally provides kits that find use in the practice of the methods of the invention.

7 Claims, 6 Drawing Sheets

Specification includes a Sequence Listing.

| Demographic Information of Subjects in the Discovery and Validation Phases | | | | | | | | |
|---|---|---|---|---|---|---|---|---|
| | | Discovery Phase | | | | Validation Phase | | |
| Demographic Variable | Characteristics | Pancreatic cancer (n=12) | Healthy control (n=12) | p | Pancreatic cancer (n=30) | Healthy control (n=30) | Chronic pancreatitis (n=30) | p |
| Age (y) | Mean ± SD | 69.42 ± 8.91 | 67.42 ± 12.44 | 0.77 | 69.6 ± 11.50 | 64.93 ± 9.74 | 54.3 ± 10.65 | <0.001 |
| Gender | Male | 8 (66.7%) | 8 (66.7%) | 1 | 19 (63.3%) | 19 (66.7%) | 16 (53.3%) | 0.766 |
| | Female | 4 (33.4%) | 4 (33.4%) | 1 | 11 (36.7%) | 11 (33.3%) | 14 (46.7%) | |
| Ethnicity | Caucasian | 9 (75%) | 9 (75%) | 1 | 20 (60%) | 20 (60%) | 20 (66.6%) | 1 |
| | African American | 0 (0.0%) | 0 (0.0%) | 1 | 2 (13.3%) | 2 (13.3%) | 2 (6.7%) | |
| | Asian | 1 (8.3%) | 1 (8.3%) | 1 | 4 (13.3%) | 4 (13.3%) | 4 (13.3%) | |
| | Hispanic | 2 (16.7%) | 2 (16.7%) | 1 | 4 (13.4%) | 4 (13.4%) | 4 (13.4%) | |
| Smoking | | | | | 5 | 2 | 12 | 0.008 |
| Drinking | | 1 | | | 2 | 3 | 3 | 1 |

*FIG. 3*

Quantitative PCR results of eleven validated mRNA biomarkers in saliva

| Gene symbol | Pancreatic cancer vs. Healthy control | | | Pancreatic cancer vs. Chronic pancreatitis | | | Pancreatic cancer vs. non-cancer | | |
|---|---|---|---|---|---|---|---|---|---|
| | P | AUC | Fold change | P | AUC | Fold change | P | AUC | Fold change |
| MBD3L2 | <0.001 | 0.788 | 8.0 ↑ | 0.003 | 0.718 | 4.3 ↑ | <0.001 | 0.754 | 5.9 ↑ |
| KRAS | <0.001 | 0.823 | 6.1 ↑ | 0.001 | 0.759 | 4.2 ↑ | <0.001 | 0.791 | 5.1 ↑ |
| STIM2 | <0.001 | 0.759 | 4.3 ↑ | 0.002 | 0.733 | 3.1 ↑ | <0.001 | 0.746 | 3.7 ↑ |
| DMXL2 | 0.007 | 0.699 | 4.6 ↑ | 0.106 | 0.622 | 2.8 ↑ | <0.001 | 0.661 | 3.1 ↑ |
| ACRV1 | <0.001 | 0.745 | 3.9 ↑ | <0.001 | 0.753 | 4.9 ↑ | <0.001 | 0.749 | 4.4 ↑ |
| DMD | <0.001 | 0.758 | 4.1 ↑ | 0.003 | 0.718 | 2.9 ↑ | <0.001 | 0.738 | 3.4 ↑ |
| CABLES1 | <0.001 | 0.783 | 4.1 ↑ | 0.003 | 0.721 | 2.7 ↑ | <0.001 | 0.753 | 3.4 ↑ |
| TK2 | 0.002 | 0.731 | 4.7 ↓ | 0.015 | 0.682 | 4.5 ↓ | 0.001 | 0.707 | 4.6 ↓ |
| GLTSCR2 | <0.001 | 0.785 | 4.8 ↓ | <0.001 | 0.769 | 5.4 ↓ | <0.001 | 0.777 | 5.1 ↓ |
| CDKL3 | 0.014 | 0.682 | 3.8 ↓ | 0.035 | 0.659 | 4.5 ↓ | 0.009 | 0.671 | 4.1 ↓ |
| TPT1 | 0.003 | 0.720 | 2.0 ↓ | 0.061 | 0.641 | 0.7 ↓ | 0.005 | 0.681 | 1.9 ↓ |
| DPM1 | 0.004 | 0.712 | 2.6 ↓ | 0.123 | 0.617 | 0.6 ↓ | 0.011 | 0.665 | 2.4 ↓ |

*FIG. 4*

Quantitative PCR results of six confirmed bacterial biomarkers in saliva pellet (n = 83)

| Strain | Pancreatic cancer vs. Healthy control | | | Pancreatic cancer vs. Chronic pancreatitis | | | Pancreatic cancer vs. non-cancer | | |
|---|---|---|---|---|---|---|---|---|---|
| | P | AUC | Fold change | P | AUC | Fold change | P | AUC | Fold change |
| A. parvulum | 0.841 | 0.551 | | 0.113 | 0.586 | | 0.308 | 0.568 | |
| G. adiacens | 0.172 | 0.575 | | 0.041 | 0.512 | 3.5 ↑ | 0.019 | 0.544 | 2.3 ↑ |
| N. elongata | 0.016 | 0.657 | 2.8 ↓ | 0.766 | 0.517 | | 0.101 | 0.588 | |
| P. nigrescens | 0.099 | 0.599 | | 0.151 | 0.634 | | 0.815 | 0.515 | |
| S. australis | 0.293 | 0.546 | | 0.122 | 0.611 | | 0.653 | 0.531 | |
| S. mitis | 0.016 | 0.680 | 2.5 ↓ | 0.012 | 0.685 | 2.1 ↓ | 0.002 | 0.682 | 2.3 ↓ |

*FIG. 5*

| Combination of salivary biomarkers for pancreatic cancer selected by logistic regression model | | | | |
|---|---|---|---|---|
| Biomarker combination | AUC | Sensitivity | Specificity | 95% CI |
| Pancreatic cancer vs. Healthy control (N. elongata and S. mitis) | 0.895 | 0.964 | 0.821 | 0.784 to 0.961 |
| Pancreatic cancer vs. Healthy control (KRAS, MBD3L2, ACRV1 and CDKL3) | 0.973 | 0.933 | 1.000 | 0.895 to 0.997 |
| Pancreatic cancer vs. Chronic pancreatitis (G. adiacens and S. mitis) | 0.700 | 0.857 | 0.556 | 0.561 to 0.816 |
| Pancreatic cancer vs. Chronic pancreatitis (CDKL3, MBD3L2, KRAS) | 0.981 | 0.967 | 0.967 | 0.907 to 0.997 |
| Pancreatic cancer vs. non-cancer (G. adiacens and S. mitis) | 0.682 | 0.857 | 0.527 | 0.571 to 0.780 |
| Pancreatic cancer vs. non-cancer (KRAS, MBD3L2, ACRV1 and DPM1) | 0.971 | 0.900 | 0.950 | 0.911 to 0.994 |

*FIG. 6*

SALIVARY TRANSCRIPTOMIC AND MICROBIAL BIOMARKERS FOR PANCREATIC CANCER

CROSS-REFERENCES TO RELATED APPLICATIONS

This application claims priority to U.S. Provisional Application Ser. No. 61/220,482, filed on Jun. 25, 2009, which is incorporated herein by reference in its entirety.

STATEMENT AS TO RIGHTS TO INVENTIONS MADE UNDER FEDERALLY SPONSORED RESEARCH OR DEVELOPMENT

This invention was made with Government support under DE016275, awarded by the National Institutes of Health. The Government has certain rights in the invention.

REFERENCE TO A "SEQUENCE LISTING," A TABLE, OR A COMPUTER PROGRAM LISTING APPENDIX SUBMITTED ON A COMPACT DISK

The sequence listing contained in the file named "008074-5029 Sequence Listing.txt", created on Jul. 30, 2010 and having a size of 37.9 kilobytes, has been submitted electronically herewith via EFS-Web, and the contents of the txt file are hereby incorporated by reference in their entirety.

BACKGROUND OF THE INVENTION

Pancreatic cancer is a disease that accounts for an estimated 43,000 cases and 36,000 deaths in the United States every year and is the $4^{th}$ leading cause of cancer deaths among both men and women in the United States. Ductal adenocarcinomas are the most common form of pancreatic cancer, and about 80% of adenocarcinomas occur at the head of the pancreas, where they frequently cause obstructive jaundice (a blockage of the bile ducts). Pancreatic cancer can also cause severe upper abdominal pain; weight loss; splenic vein obstruction, resulting in splenomegaly, gastric and esophageal varices, and GI hemorrhage; and diabetes.

In over 90% of patients with pancreatic cancer, diagnosis does not occur until a late stage of cancer, because the disease is usually asymptomatic at early stages. Frequently, by the time patients present with symptoms of pancreatic cancer and are diagnosed with the disease, the cancer has spread to regional lymph nodes or metastasized to the liver or lung. Although the prognosis for patients diagnosed with pancreatic cancer varies with stage, the overall prognosis for the disease is poor, and less than 4% of all patients survive longer than 5 years, due in part to the fact that patients generally have an advanced stage of the disease at the time of diagnosis. About 80-90% of pancreatic cancers are surgically unresectable by the time of diagnosis because of metastasis or invasion of blood vessels. Therefore, the treatment options that are available for most pancreatic cancer patients are more limited than they would be if earlier detection of pancreatic cancer were available. Thus, detection of pancreatic cancer at an early stage would likely improve the mortality rates associated with this disease[1-3].

Biomarkers are measurable biological and physiological parameters that can serve as indices for health-related assessments, such as diagnosis of disease. Nucleic acid and protein biomarkers are especially useful because they are amenable to bodily fluid tests (such as saliva tests), which are easier and more convenient to administer than tissue biopsy tests. With respect to detecting early stage pancreatic cancer, however, the current biomarkers and testing strategies that exist[1,4-8] are limited in their usefulness because they are either confined to a small number of patients at greater risk, rely on invasive procedures, or lack the necessary sensitivity and specificity to be suitable for widespread screening[9-11]. For example, pancreas-associated antigen CA 19-9 is used to screen patients who are at high risk of developing pancreatic cancer, but it is not sensitive or specific enough to be suitable for general population screening. Additionally, the search for potential useful biomarkers of pancreatic cancer is further complicated by the existence of several benign pancreatic diseases, such as chronic pancreatitis, which has phenotypic overlap with early stage pancreatic cancer. In particular, the lack of specificity of currently used pancreatic cancer biomarkers is often due to the presence of these biomarkers in patients with chronic pancreatitis[4,5].

Saliva has gained attention as a diagnostic fluid because it is simple to collect and readily accessible via a non-invasive procedure. Salivary constituents including DNA, RNA, protein, and bacteria have been studied as potential diagnostic markers for various diseases, such as oral disease[15,16 17 18] and systemic disease[19 20 21 22].

Given the importance of early detection for successful treatment of pancreatic cancer, and given the limitations of the currently existing strategies for detecting pancreatic cancer at an early stage, there is a need in the field for biomarkers of pancreatic cancer, and methods of using such biomarkers, that are minimally invasive and also sensitive and specific enough in detecting early-stage pancreatic cancer to be suitable for widespread screening of patients. The present invention addresses this need and others.

BRIEF SUMMARY OF THE INVENTION

In one aspect, the present invention provides a method of diagnosing pancreatic cancer in a subject, the method comprising the steps of (a) analyzing a saliva sample from the subject with an assay that specifically detects a marker selected from the group consisting of a nucleic acid or polypeptide encoded by a nucleic acid listed in FIG. 4; and (b) comparing the level of expression of the marker to a control to determine whether or not the marker is differentially expressed in the sample as compared to the control; thereby providing a diagnosis for pancreatic cancer.

In one embodiment, the analyzing step comprises analyzing the saliva sample from the subject with an assay that specifically detects the markers KRAS, MBD3L2, ACRV1, and DPM1, and wherein the comparing step comprises determining whether or not KRAS, MBD3L2, ACRV1, and DPM1 are differentially expressed in the sample. In one embodiment, the marker distinguishes between chronic pancreatitis and pancreatic cancer. In one embodiment, the markers are CDKL, MBD3L2, and KRAS and they are all detected.

In another aspect, the present invention provides a method of diagnosing pancreatic cancer in a subject, the method comprising the steps of: (a) analyzing a saliva sample from the subject with an assay that specifically detects a marker selected from the group consisting of a microbe listed in FIG. 5; and (b) comparing the amount of the marker to a control to determine whether or not the marker is increased or decreased in the sample as compared to the control; thereby providing a diagnosis for pancreatic cancer.

In one embodiment, the analyzing step comprises analyzing the saliva sample from the subject with an assay that specifically detects *Neisseria elongate* and *Streptococcus mitis* or *Granulicatella adiacens* and *Streptococcus mitis*, and wherein the comparing step comprises determining whether or not the levels of *Neisseria elongate* and *Streptococcus mitis* or *Granulicatella adiacens* and *Streptococcus mitis* have increased or decreased in the sample relative to a control. In one embodiment, the marker distinguishes between chronic pancreatitis and pancreatic cancer. In one embodiment, the markers are *Granulicatella adiacens* and *Streptococcus mitis* and they are both detected.

In one embodiment, the assay detects more than one marker. In one embodiment, the assay detects protein and is ELISA, Western blotting, flow cytometry, immunofluorescence, immunohistochemistry, or mass spectroscopy. In one embodiment, the assay detects nucleic acid and is mass spectroscopy, PCR, microarray hybridization, thermal cycle sequencing, capillary array sequencing, or solid phase sequencing.

In one embodiment, the assay comprises a reagent that binds to a protein. In one embodiment, the reagent is an antibody. In one embodiment, the reagent is a monoclonal antibody. In one embodiment, the assay comprises a reagent that binds to a protein and the assay is ELISA, Western blotting, flow cytometry, immunofluorescence, immunohistochemistry, or mass spectroscopy.

In one embodiment, the assay comprises a reagent that binds to a nucleic acid. In one embodiment, the reagent is a nucleic acid. In one embodiment, the reagent is an oligonucleotide. In one embodiment, the reagent is an RT-PCR primer set.

In yet another aspect, the present invention provides a kit for diagnosing pancreatic cancer in a subject, the kit comprising a reagent that specifically detects a marker selected from the group consisting of a nucleic acid or polypeptide encoded by a nucleic acid listed in FIG. 4.

In one embodiment, the kit comprises reagents that specifically detect the markers KRAS, MBD3L2, ACRV1, and DPM1.

In still another aspect, the present invention provides a kit for diagnosing pancreatic cancer in a subject, the kit comprising a reagent that specifically detects marker selected from the group consisting of a microbe listed in FIG. 5.

In one embodiment, the kit comprises reagents that specifically detect the markers *Granulicatella adiacens* and *Streptococcus mitis*.

BRIEF DESCRIPTION OF THE DRAWINGS

FIG. 3. Demographic information (age, gender, ethnicity, smoking history, and drinking history) for subjects in the discovery and validation phases. For the validation samples, p-value was calculated among three groups. Detailed information on individual characteristics is presented in Table A1.

FIG. 4. Quantitative PCR results of eleven validated mRNA biomarkers in saliva. Quantitative PCR was used to validate the microarray findings on an independent clinical sample set, including saliva from 30 pancreatic cancer patients, 30 healthy control subjects, and 30 chronic pancreatitis patients. Wilcoxon Signed Rank test: if P<0.05, the marker is validated. "↑" (upwards-facing arrow): upregulated in pancreatic cancer; "↓," (downwards-facing arrow): downregulated in pancreatic cancer.

FIG. 5. Quantitative PCR results of six confirmed bacterial biomarkers in saliva pellet (n=83). Quantitative PCR was performed to validate the HOMIM microarray findings on an independent clinical sample set, including saliva from 28 pancreatic cancer patients (Pc), 28 healthy control subjects (normal), and 27 chronic pancreatitis patients (Pt). Wilcoxon Signed Rank test: if P<0.05, the marker is validated. "↑" (upwards-facing arrow): upregulated in pancreatic cancer; "↓," (downwards-facing arrow): downregulated in pancreatic cancer. Fold change is only shown for the validated biomarkers.

FIG. 6. Combination of salivary biomarkers for pancreatic cancer selected by logistic regression model. The logistic regression model was built based on the validated mRNA biomarkers or validated bacterial biomarkers for distinguishing pancreatic cancer from healthy controls, pancreatic cancer from chronic pancreatitis, and pancreatic cancer from the non-cancer group. The best models for each comparison, providing the highest discriminatory power with the simplest combination, are shown with the symbol of each biomarkers. Abbreviations: 95% CI=95% confidence interval; P=significance level P (area=0.5).

DETAILED DESCRIPTION OF THE INVENTION

I. Introduction

Figure 1:
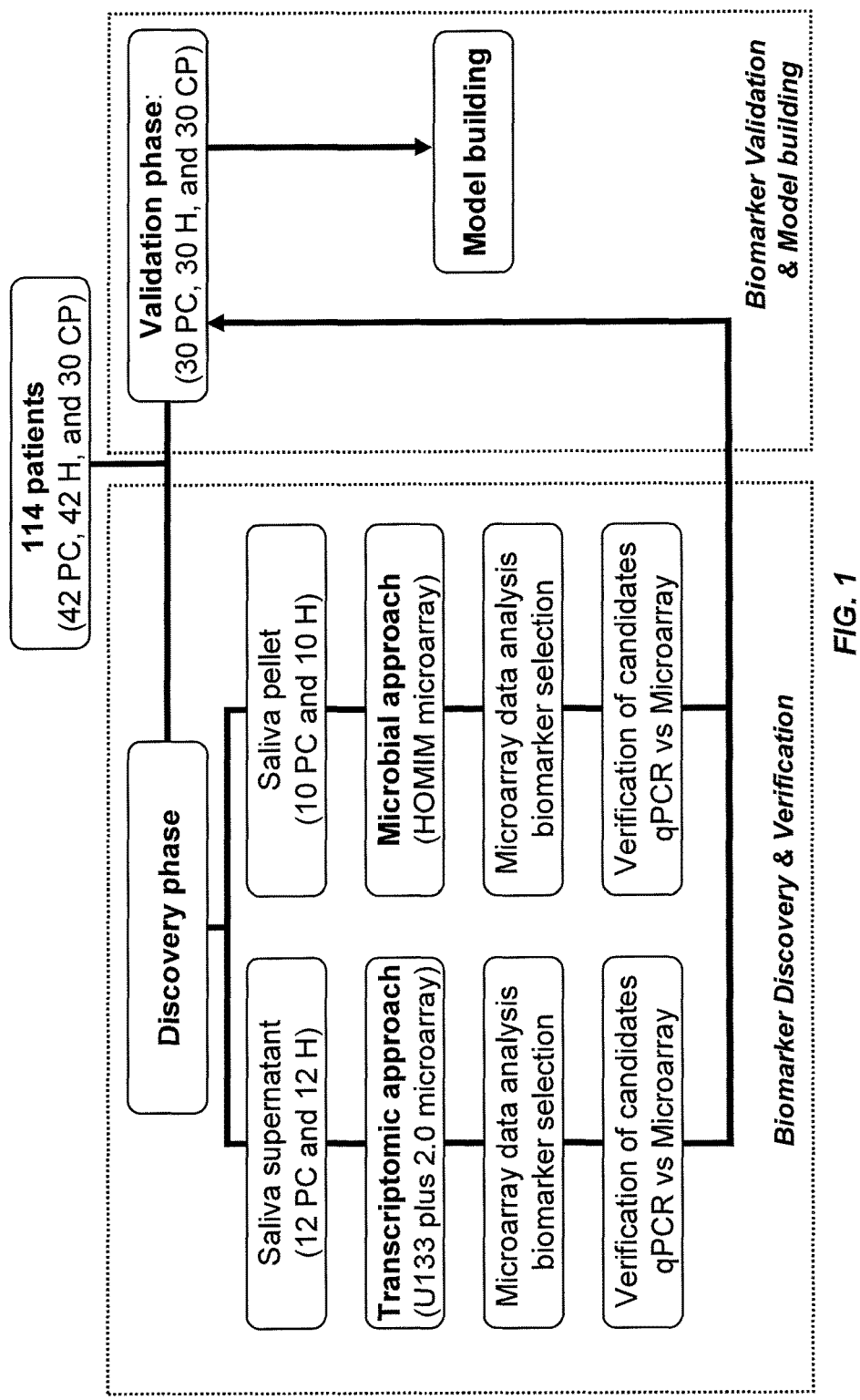
FIG. 1. Schematic of the strategy used for the discovery and validation of salivary biomarkers.

The present invention relates to the discovery of novel nucleic acid and microbial pancreatic cancer biomarkers in saliva and novel methods of using such biomarkers for diagnosing pancreatic cancer. The present invention also provides kits useful in the practice of the methods of the invention.

Pancreatic cancer generally has a poor prognosis, with a five-year life expectancy of less than about 4%, due in part to the late onset of symptoms of pancreatic cancer, frequently after the cancer has metastasized or become surgically unresectable. Therefore, methods of diagnosing pancreatic cancer at an early stage, prior to the point in which the cancer has metastasized or become surgically unresectable, would likely lead to improved outcomes and higher life expectancy rates for individuals having pancreatic cancer. However, the methods of diagnosing pancreatic cancer should be specific enough to distinguish between pancreatic cancer and chronic pancreatitis, a chronic inflammation of the pancreas that is a risk factor for later developing pancreatic cancer, but which is not cancer and does not always lead to cancer.

We performed high-throughput analyses of the salivary transcriptome and salivary microbial profiles of samples from individuals with pancreatic cancer, individuals with chronic pancreatitis, and healthy controls. The results of these initial screens were verified by quantitative PCR, and verified candidates were subsequently independently validated by quantitative PCR, to yield twelve novel mRNA biomarkers of pancreatic cancer (including 7 genes that are upregulated in pancreatic cancer and 5 genes that are downregulated in pancreatic cancer) and three microbial markers of pancreatic cancer (including 2 microbes that are downregulated in pancreatic cancer and one microbe that is upregulated in pancreatic cancer).

To test the prediction/classification power of these biomarkers, logistic model and receiver operating characteristic curve (ROC) analysis were performed based on the validated results. A combination of four mRNA biomarkers (KRAS, MBD3L2, ACRV1, and CDKL3) is highly sensitive and specific for distinguishing pancreatic cancer patients from healthy subjects (ROC-plot area under the curve (AUC) value of 0.973; 93.3% sensitivity; 100% specificity), as is a combination of two bacterial biomarkers (*N. elongata* and *S. mitis*) (ROC-plot AUC value of 0.895; 96.4% sensitivity; 82.1% specificity). Additionally, the combination of mRNA biomarkers KRAS, MBD3L2, and CDKL3 is highly sensitive and specific for distinguishing pancreatic cancer patients from patients with chronic pancreatitis (ROC-plot AUC value of 0.981; 96.7% sensitivity; 96.7% specificity). Furthermore, a four-marker logistic regression model using the mRNA biomarkers KRAS, MBD3L2, ACRV1, and CDKL3 provided the highest discriminatory power for differentiating pancreatic cancer subjects from non-cancer subjects (ROC-plot AUC value of 0.971, 90.0% sensitivity, 95.0% specificity using a cutoff of 0.433). Thus, our results provide novel biomarkers and combinations of biomarkers for the detection of pancreatic cancer.

II. Definitions

As used herein, the following terms have the meanings ascribed to them unless specified otherwise.

The terms "biomarker" or "pancreatic cancer biomarker" interchangeably refer to a gene, mRNA, protein, or microbe that is present in a biological sample, e.g. saliva, from a subject with a disease, such as pancreatic cancer, at a different level or concentration in comparison to a biological sample from a subject without the disease, and which is useful for the diagnosis of the disease, for providing a prognosis, or for preferential targeting of a pharmacological agent to an affected cell or tissue.

Pancreatic cancer biomarkers recited herein refer to polypeptides, nucleic acids, and microbes, e.g., gene, pre-mRNA, mRNA, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; or (4) have a nucleic acid sequence that has greater than about 60% nucleotide sequence identity, 65%, 70%, 75%, 80%, 85%, 90%, preferably 91%, 92%, 93%, 94%, 95%, 96%, 97%, 98% or 99% or higher nucleotide sequence identity, preferably over a region of at least about 10, 15, 20, 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

Biomarkers of the invention may be identified by gene name, e.g., v-Ki-ras2 Kirsten rat sarcoma viral oncogene homolog; gene symbol, e.g., KRAS; locus in the human genome, e.g. 12p12.1; Genbank accession number, e.g., NM_004985; or the like. It is understood that all of these identifiers reference the same biomarker and thus are equivalent. Salivary transcriptome biomarkers of the invention are identified in Table 4 below, and include: ACRV1 (acrosomal vesicle protein 1; NM_001612); CDC14B (CDC14 cell division cycle 14 homolog B; NM_003671); ASH2L (ash2-like; NM_004674); STIM2 (stromal interaction molecule 2; NM_020860); GPR124 (G protein-coupled receptor 124; NM_032777); LILRA2 (leukocyte immunoglobulin-like receptor, subfamily A, member 2; NM_006866); ENG (endoglin; NM_000118); RMB24 (RNA binding motif protein 24; NM_153020); LRRK1 (leucine-rich repeat kinase 1; NM_024652); DMXL2 (Dmx-like 2; NM_015263); ZSCAN16 (zinc finger and SCAN domain containing 16; NM_025231); MBD3L2 (methyl-CpG binding domain protein 3-like 2; NM_144614); GPX3 (glutathione peroxidase 3; NM_002084); ITGA2B (integrin, alpha 2b; NM_000419); CDH4 (cadherin 4; NM_001794); S100P (S100 calcium binding protein P; NM_005980); FTHP1 (ferritin, heavy polypeptide pseudogene 1; NG_005639); ZMIZ2 (zinc finger, MIZ-type containing 2; NM_031449); DDX3X (DEAD (Asp-Glu-Ala-Asp; SEQ ID NO: 161) box polypeptide 3, X-linked; NM_001356); UTF1 (undifferentiated embryonic cell transcription factor 1; NM_003577); KRAS (v-Ki-ras2 Kirsten rat sarcoma viral oncogene homolog; NM_004985); DMD (dystrophin; NM_000109); CABLES1 (Cdk5 and Abl enzyme substrate 1; NM_001100619); TPT1 (tumor protein, translationally-controlled 1; NM_003295); MARCKS (myristoylated alanine-rich protein kinase C substrate; NM_002356); SAT1 (spermidine/spermine N1-acetyltransferase 1; NM_002970); PNPLA8 (patatin-like phospholipase domain containing 8; NM_015723); DPM1 (dolichyl-phosphate mannosyltransferase polypeptide 1; NM_003859); CD7 (CD7 molecule; NM_006137); PCSK6 (proprotein convertase subtilisin/kexin type 6; NM_138319); TK2 (thymidine kinase 2; NM_004614); FTH1 (ferritin, heavy polypeptide 1; NM_002032); TUBA1A (tubulin, alpha 1b; NM_006082); GLTSCR2 (glioma tumor suppressor candidate region gene 2; NM_0015710); and CDKL3 (cyclin-dependent kinase-like 3; NM_016508).

Alternatively, biomarkers of the invention may be identified by the name of a "microbe," or microscopic unicellular organism. Microbial biomarkers of the invention are identified in FIG. 5, and include: *Atopobium parvulum* (*A. parvulum*), *Granulicatella adiacens* (*G. adiacens*), *Neisseria elongata* (*N. elongata*), *Prevotella nigrescens* (*P. nigrescens*), *Streptococcus australis* (*S. australis*), and *Streptococcus mitis* (*S. mitis*).

The term "cancer" refers to human cancers and carcinomas, sarcomas, adenocarcinomas, lymphomas, leukemias, solid and lymphoid cancers, etc. Examples of different types of cancer include, but are not limited to, pancreatic cancer, breast cancer, gastric cancer, bladder cancer, oral cancer, ovarian cancer, thyroid cancer, lung cancer, prostate cancer, uterine cancer, testicular cancer, neuroblastoma, squamous cell carcinoma of the head, neck, cervix and vagina, multiple myeloma, soft tissue and osteogenic sarcoma, colorectal cancer, liver cancer (i.e., hepatocarcinoma), renal cancer (i.e., renal cell carcinoma), pleural cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, and acute myelocytic leukemia. Cancers embraced in the current application include both metastatic and non-metastatic cancers.

As used herein, "pancreatic cancer" refers to a group of malignant or neoplastic cancers originating in the pancreas of an individual. Non-limiting examples of pancreatic cancers include adenocarcinomas (e.g., ductal adenocarcinoma and acinar cell adenocarcinoma), adenosquamous carcinomas, squamous cell carcinomas, giant cell carcinomas, cystadenocarcinomas, and pancreatic neuroendocrine carcinomas.

"Metastasis" refers to spread of a cancer from the primary tumor or origin to other tissues and parts of the body, such as the lymph nodes.

"Saliva" refers to any watery discharge from the mouth, nose, or throat. For the purposes of this invention, saliva may include sputum and nasal or post nasal mucous.

"Diagnosis" refers to identification of a disease state, such as cancer or chronic pancreatitis, in a subject. The methods of diagnosis provided by the present invention can be combined with other methods of diagnosis well known in the art. Non-limiting examples of other methods of diagnosis include, detection of known disease biomarkers in saliva samples, oral radiography, co-axial tomography (CAT) scans, positron emission tomography (PET), radionuclide scanning, oral biopsy, and the like.

"Providing a prognosis" refers to providing a prediction of the likelihood of metastasis, predictions of disease free and overall survival, the probable course and outcome of cancer therapy, or the likelihood of recovery from the cancer, in a subject.

The term "differentially expressed" or "differentially regulated" refers generally to a protein or nucleic acid that is overexpressed (upregulated) or underexpressed (downregulated) in one biological sample compared to at least one other sample, generally in saliva from a subject with cancer or a cancer cell, in comparison to saliva from a subject without cancer or a non-cancer cell, in the context of the present invention.

The terms "overexpress," "overexpression," "overexpressed," "upregulate," or "upregulated" interchangeably refer to a biomarker that is present at a detectably greater level in a biological sample, e.g. saliva or cancer cell, from a patient with cancer, in comparison to a biological sample from a patient without cancer. The term includes overexpression in a sample from a patient with cancer due to transcription, post transcriptional processing, translation, post-translational processing, cellular localization (e.g, organelle, cytoplasm, nucleus, cell surface), and RNA and protein stability, as compared to a sample from a patient without cancer. Overexpression can be 10%, 20%, 30%, 40%, 50%, 60%, 70%, 80%, 90% or more in comparison to a sample from a patient without cancer. In certain instances, overexpression is 1-fold, 2-fold, 3-fold, 4-fold 5, 6, 7, 8, 9, 10, or 15-fold or more higher levels of transcription, translation, or microbe presence in comparison to a sample from a patient without cancer.

The terms "underexpress," "underexpression," "underexpressed," "downregulate," or "downregulated" interchangeably refer to a biomarker that is present at a detectably lower level in a biological sample, e.g. saliva or cancer cell, in comparison to a biological sample from a subject without cancer. The term includes underexpression due to transcription, post transcriptional processing, translation, post-translational processing, cellular localization (e.g., organelle, cytoplasm, nucleus, cell surface), and RNA and protein stability, as compared to a control. Underexpression can be 10%, 20%, 30%, 40%, 50%, 60%, 70%, 80%, 90% or less in comparison to a sample from a subject without cancer. In certain instances, underexpression is 1-fold, 2-fold, 3-fold, 4-fold or more lower levels of transcription, translation or microbe presence in comparison to a control. Overexpression and underexpression can be detected using conventional techniques for detecting mRNA (e.g., RT-PCR, PCR, hybridization), proteins (e.g., ELISA, immunohistochemical techniques, mass spectroscopy, Luminex® xMAP technology), or microbes (e.g., microbial nucleic acid profiling).

It will be understood by the skilled artisan that markers may be used singly or in combination with other markers for any of the uses, e.g., diagnosis or prognosis of pancreatic cancer.

"Disease transcriptome," "pancreatic cancer transcriptome," or "salivary pancreatic transcriptome" refers to a set of genes differentially expressed in a biological sample from an individual or group of individuals suffering from a given disease. Disease transcriptomes may be derived from a particular biological sample, i.e. saliva as in the scope of the present invention. Many disease transcriptomes are known in the art, as are methods of determining a disease transcriptome (see, e.g., U.S. Pat. Nos. 7,229,774, 7,378,239, 7,378,236, 6,833,247, and 7,171,311).

As used herein, an "expression profile" refers to the quantitative or qualitative level of a biomarker found in a transcriptome, such as a control or salivary pancreatic cancer transcriptome, or the quantitative or qualitative level of a microbial biomarker. A salivary pancreatic cancer expression profile may comprise, for example, the quantitative or qualitative level of nucleic acid or protein of one or more transcriptome and/or microbial biomarkers that are differentially expressed in the saliva of an individual having pancreatic cancer as compared to an individual who does not have pancreatic cancer (e.g., a healthy control, a non-cancer control, and/or a control having chronic pancreatitis).

"Biological sample" includes sections of tissues such as biopsy and autopsy samples, and frozen sections taken for histologic purposes. Such samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, or mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.*, 2:482 (1981), by the homology alignment algorithm of Needleman & Wunsch, *J. Mol. Biol.*, 48:443 (1970), by the search for similarity method of Pearson & Lipman, *Proc. Nat'l. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA*, 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of proteins. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, ÿ-carboxyglutamate, and O-phosphoserine Amino acid analogs refers to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "specifically (or selectively) binds" or "specifically (or selectively) detects" refers to a binding reaction that is determinative of the presence of a marker, such as a protein, nucleic acid, or microbe, which is often in a heterogeneous population of proteins, nucleic acids, or microbes and other biologics. For example, the presence of a protein is specifically detected if, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Luminex® xMAP technology is particularly well suited for the present invention. Similarly, the presence of a nucleic acid (or of a microbe, the presence of which can be determined by analyzing the nucleic acid content of the microbe) is specifically detected if, under designated hybridization conditions, the specified oligonucleotides bind to a particular nucleic acid target sequence at least two times the background and more typically more than 10 to 100 times background. Specific binding to an oligonucleotide under such conditions requires an oligonucleotide that is selected for its specificity for a particular nucleic acid sequence. For example, oligonucleotides can be selected which bind to the target nucleic acid sequence under stringent hybridization conditions.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications* (Academic Press, Inc., N.Y., 1990).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$ a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature, 348:552-554 (1990)).

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

III. Diagnostic and Prognostic Methods

The present invention provides methods of diagnosing a pancreatic cancer by examining protein or RNA expression of transcriptome or microbe biomarkers listed in FIGS. 4 and 5 and in Table 4, or a combination thereof, including wild-type, truncated or alternatively spliced forms, in biological samples. Diagnosis involves determining the level of a polynucleotide or polypeptide of the invention in a patient and then comparing the level to a baseline or range. Typically, the baseline value is representative of a polynucleotide or polypeptide of the invention in a healthy person not suffering from cancer, as measured using biological sample such as a tissue sample (e.g., tongue or lymph tissue), serum, blood, or saliva. Variation of levels of a polynucleotide or polypeptide of the invention from the baseline range (either up or down) indicates that the patient has a pancreatic cancer.

PCR assays such as Taqman® allelic discrimination assay available from Applied Biosystems can be used to identify RNA. In another embodiment, mass spectroscopy can be used to detect either nucleic acid or protein. Any antibody-based technique for determining a level of expression of a protein of interest can be used. For example, immunoassays such as ELISA, Western blotting, flow cytometry, immunofluorescence, and immunohistochemistry can be used to detect protein in patient samples. Combinations of the above methods, such as those employed in the Luminex® xMAP technology can also be used in the present invention.

Analysis of a protein or nucleic acid can be achieved, for example, by high pressure liquid chromatography (HPLC), alone or in combination with mass spectrometry (e.g., MALDI/MS, MALDI-TOF/MS, tandem MS, etc.).

Analysis of nucleic acid can be achieved using routine techniques such as northern analysis, reverse-transcriptase polymerase chain reaction (RT-PCR), microarrays, sequence analysis, or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al., Theophilus et al., and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Non-limiting examples of sequence analysis include Sanger sequencing, capillary array sequencing, thermal cycle sequencing (Sears et al., *Biotechniques,* 13:626-633 (1992)), solid-phase sequencing (Zimmerman et al., *Methods Mol. Cell Biol.,* 3:39-42 (1992)), sequencing with mass spectrometry such as matrix-assisted laser desorption/ionization time-of-flight mass spectrometry (MALDI-TOF/MS; Fu et al., *Nature Biotech.,* 16:381-384 (1998)), and sequencing by hybridization (Chee et al., *Science,* 274:610-614 (1996); Drmanac et al., *Science,* 260:1649-1652 (1993); Drmanac et al., *Nature Biotech.,* 16:54-58 (1998)). Non-limiting examples of electrophoretic analysis include slab gel electrophoresis such as agarose or polyacrylamide gel electrophoresis, capillary electrophoresis, and denaturing gradient gel electrophoresis A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.,* 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis,* 18:2184-93 (1997); Bao, *J. Chromatogr. B. Biomed. Sci.,* 699:463-80 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.,* 27:261-276 (1989)).

Specific immunological binding of the antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine, Indirect labels include various enzymes well known in the art, such as horseradish peroxidase (HRP), alkaline phosphatase (AP), ÿ-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a ÿ-galactosidase detection system can be used with the chromogenic substrate o-nitrophenyl-ÿ-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

IV. Compositions, Kits, and Arrays

The invention provides compositions, kits and integrated systems for practicing the assays described herein using polynucleotides and polypeptides of the invention, antibodies specific for polypeptides or polynucleotides of the invention, etc.

The invention provides assay compositions for use in solid phase assays; such compositions can include, for example, one or more polynucleotides or polypeptides of the invention immobilized on a solid support, and a labeling reagent. In each case, the assay compositions can also include additional reagents that are desirable for hybridization. Modulators of expression or activity of polynucleotides or polypeptides of the invention can also be included in the assay compositions.

The invention also provides kits for carrying out the diagnostic assays of the invention. The kits typically include a probe that comprises an antibody or nucleic acid sequence that specifically binds to polypeptides or polynucleotides of the invention, and a label for detecting the presence of the probe. The kits may include several polynucleotide sequences encoding polypeptides of the invention.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical images.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g., by fluorescent or dark field microscopic techniques.

V. Examples

The following examples are offered to illustrate, but not to limit, the claimed invention.

Here, we report the use of two high throughput discovery approaches to identify discriminatory biomarkers in saliva for the non-invasive detection of early stage pancreatic cancer. Our results demonstrate that the profiles of salivary transcriptome and microflora are significantly different between patients with early stage pancreatic cancer and healthy controls. The salivary biomarkers identified and validated in these platforms possess great discriminatory power for the detection of early stage pancreatic cancer, with high specificity and sensitivity.

Patients and Methods

Patients.

This study, which was approved by the UCLA Institutional Review Board, started sample collection in February 2006. It had a discovery phase, followed by an independent validation phase. All subjects with clinically diagnosed pancreatic cancer, chronic pancreatitis and healthy control were recruited from the UCLA Medical Center. The saliva bank of pancreatic disease at the UCLA Dental Research Institute has collected 283 saliva samples since 2006. Of these, 114 samples, from 42 pancreatic cancer patients, 30 chronic pancreatitis patients and 42 healthy control individuals (Table 1), were selected for the discovery and validation phase of this study. Inclusion criteria of disease patients consisted of confirmed diagnosis of primary disease (stage I pancreatic cancer and chronic pancreatitis). Exclusion criteria included chemotherapy or radiation therapy prior to saliva collection and a diagnosis of other malignancies within 5 y from the time of saliva collection. Written informed consents and questionnaire data sheets were obtained from all patients who agreed to serve as saliva donors. The information on individual characteristics, such as age, gender, ethnicity, smoking history and drinking history, is presented in FIG. 3. Healthy control individuals were matched for age, gender and ethnicity to the cancer group. Unstimulated saliva samples were collected and processed as previously described[12,23]. Both supernatant and pellet samples were reserved at −80° C. prior to assay.

Study Design.

Of the 114 samples, 12 pancreatic cancer samples and 12 healthy control samples were chosen for the discovery phase. The transcriptomic approach profiled the saliva supernatant samples from 12 pancreatic cancer patients and 12 healthy control subjects using the Affymetrix HG U133 Plus 2.0 Array. The microbial approach profiled the saliva pellet samples from 10 pancreatic cancer patients and 10 healthy control subjects using the Human Oral Microbe Identification Microarray (HOMIM) platform[24]. Biomarkers identified from both platforms were first verified using the discovery sample set. An independent sample set, including 30 pancreatic cancer patients, 30 chronic pancreatitis patients and 30 healthy control subjects, was used for the biomarker validation phase (FIG. 1).

Salivary Transcriptomic Profiling.

RNA was isolated from 330 μL of saliva supernatant using the MagMax™ Viral RNA Isolation Kit (Ambion, Austin, Tex.). This process was automated using KingFisher mL technology (Thermo Fisher Scientific), followed by TURBO™ DNase treatment (Ambion). Extracted RNA was linearly amplified using the RiboAmp RNA Amplification kit (Molecular Devices, Sunnyvale, Calif.). After purification, cDNA was in vitro transcribed and biotinylated using GeneChip Expression 3'-Amplification Reagents for in vitro transcription labeling (Affymetrix, Santa Clara, Calif.). Chip hybridization and scanning were performed at the UCLA microarray core facility.

U133 Plus 2.0 Array Data Analysis.

The analysis was performed using R 2.7.0 (http://www.r-project.org). The Probe Logarithmic Intensity Error Estimation (PLIER) expression measures were computed after background correction and quantile normalization for each microarray dataset. Probeset-level quantile normalization was performed across all samples to make the effect sizes similar among all datasets. Finally, for every probeset, the two-sample t-test was applied to identify differential expression between cancer and healthy control. After obtaining the estimates and the p-values of each probeset, we corrected the p-values for false discovery rate (FDR).

Validation of mRNA Biomarkers Using Quantitative PCR (qPCR).

The selected mRNA biomarkers were first verified by qPCR using the discovery sample set (12 pancreatic cancer and 12 healthy control) as described previously[16,25]. qPCR primers were designed using Primer Express 3.0 software (Applied Biosystems, FosterCity, Calif.) (Table 2). All primers were synthesized by Sigma-Genosys (Woodlands, Tex.). The amplicons were intron spanning whenever possible. qPCR was carried out in duplicate. Verified biomarkers were then assayed by qPCR in the set of 90 independent samples. The Wilcoxon test was used to compare the biomarkers between groups.

Salivary Microflora Profiling and Microbial Biomarker Validation.

Ten pancreatic cancer pellets and 10 matched control pellets were used for the microbial profiling. Bacterial DNA was extracted using UltraClean Microbial DNA Isolation Kit (MO BIO Laboratories, Carlsbad, Calif.). PCR amplification using 16S universal primers[26] was performed at the Forsyth Institute, followed by hybridization to the Human Oral Microbe Identification Microarray (HOMIM)[24]. Selection of bacterial candidates was based on p-value by Wilcoxon rank-sum test (P<0.05). Quantities of bacterial species in the original DNA samples were determined by qPCR. Specific primers (Table 3) were designed for the 16S rRNA genes of the bacterial biomarker candidates. qPCR was carried out in duplicate in reaction volumes of 10 μL using power SYBR-Green Master Mix (Applied Biosystems, Foster City, Calif.) for 15 min at 95° C. for initial denaturing, followed by 40 cycles of 95° C. for 30 sec and 60° C. for 30 sec in the ABI 7900HT Fast Real Time PCR system (Applied Biosystems). Verified microbial biomarkers were then subjected to independent clinical validation by qPCR. The Wilcoxon test was used to compare the biomarkers between groups.

Predictive Model Building and Evaluation.

The logistic regression (LR) method was used in prediction model building. For each validated biomarker, we constructed the receiver operating characteristic (ROC) curve and computed the Area Under Curve (AUC) value by numerical integration of the ROC curve. Next, the validated salivary biomarkers were fit into logistic regression models (separately for mRNA and microbial biomarkers, and separately for each group comparisons) and stepwise backward model selection was performed to determine final combinations of biomarkers. For each of these models, the predicted probability for each subject was obtained and was used to construct ROC curves. The standard error of the AUC and the 95% confidence interval (CI) for the ROC curve was computed according to previous publications[27,28]. The sensitivity and specificity for the biomarker combinations were estimated by identifying the cutoff-point of the predicted probability that yielded the highest sum of sensitivity and specificity.

Identification and Validation of mRNA Biomarkers for Pancreatic Cancer

Transcriptomic profiling revealed that 958 genes exhibited >2 fold up-regulation and 691 genes exhibited >2 fold down-regulation in the saliva of pancreatic cancer patients, relative to the healthy controls (n=24, P<0.05). These transcripts identified were unlikely to be attributed to chance ($\chi^2$ test, P<0.0001), considering the false positive with P<0.05. Using a predefined criterion of a change in regulation >4-fold, and a more stringent cutoff of p-value <0.01, we identified 49 up-regulated and 21 down-regulated transcripts in pancreatic cancer samples.

Quantitative PCR was performed to verify the microarray results on the discovery sample set. All 49 up-regulated and 21 down-regulated transcripts were evaluated. The results confirmed that the relative RNA expression levels of 23 up-regulated and 12 down-regulated transcripts, as measured by qPCR, were consistent with the results of the microarray analysis. The biological functions of these genes and their products are presented in Table 4. These verified candidates were then subjected to an independent validation by qPCR. As shown in FIG. 4, a total of 7 up-regulated and 5 down-regulated genes were validated based on the qPCR data of 30 pancreatic cancer patients and 30 healthy control subjects. All 12 mRNA biomarkers showed significant difference between pancreatic cancer and healthy controls (P<0.05, n=60), yielding ROC-plot AUC values between 0.682 and 0.823. The expression patterns of these mRNA biomarkers were consistent with those retrieved by microarray assay (up/down-regulation and fold change). Importantly, the expression levels of six up-regulated mRNAs (MBD3L2, KRAS, STIM2, ACRV1, DMD, CABLES1) and three down-regulated mRNAs (TK2, GLTSCR2, CDKL3) were also significantly different between pancreatic cancer and chronic pancreatitis (P<0.05, n=60). The expression level of all 12 up/down-regulated mRNAs were significantly different between pancreatic cancer (n=30) and non-cancer subjects (chronic pancreatitis and healthy control, n=60) (P<0.05), yielding ROC-plot AUC values between 0.661 and 0.791 (FIG. 4).

Identification and Validation of Bacterial Biomarkers for Pancreatic Cancer

Based on the microarray data of 410 oligonucleotide probes on the HOMIM, 16 species/clusters showing significant difference between pancreatic cancer and healthy controls (P<0.05, n=20) were selected as biomarker candidates for qPCR verification of the microarray results. These 16 species/clusters represented 6 different genus, including *Streptococcus* (3 species/groups), *Prevotella* (4 species/groups), *Campylobacter* (4 species/groups), *Granulicatella* (2 species), *Atopobium* (1 species), and *Neisseria* (2 species). Using the discovery sample set, 6 out of 16 species were confirmed by qPCR (FIG. 5). These candidates were then subjected to the independent validation by qPCR (28 pancreatic cancer, 27 chronic pancreatitis and 28 healthy control. Two pancreatic cancer, 3 chronic pancreatitis and 3 healthy control samples did not have usable DNA). Two bacterial markers (*Neisseria elongata* and *Streptococcus mitis*) showed significant difference between pancreatic cancer and healthy controls (P<0.05, n=56), yielding ROC-plot AUC values of 0.657 and 0.680, respectively. The levels of both bacterial markers were decreased in pancreatic cancer as shown by qPCR, which were consistent with the results obtained by HOMIM. The levels of an increased species (*Granulicatella adiacens*) and a decreased species (*Streptococcus mitis*) were significantly different between pancreatic cancer and chronic pancreatitis (P<0.05, n=55). The levels of *G. adiacens* and *S. mitis* were also significantly different between pancreatic cancer (n=28) and non-cancer subjects (chronic pancreatitis and healthy controls, n=55) (P<0.05), yielding ROC-plot AUC values of 0.544 and 0.682, respectively (FIG. 5).

Prediction Models Using the Validated mRNA and Bacterial Biomarkers

Figure 2:
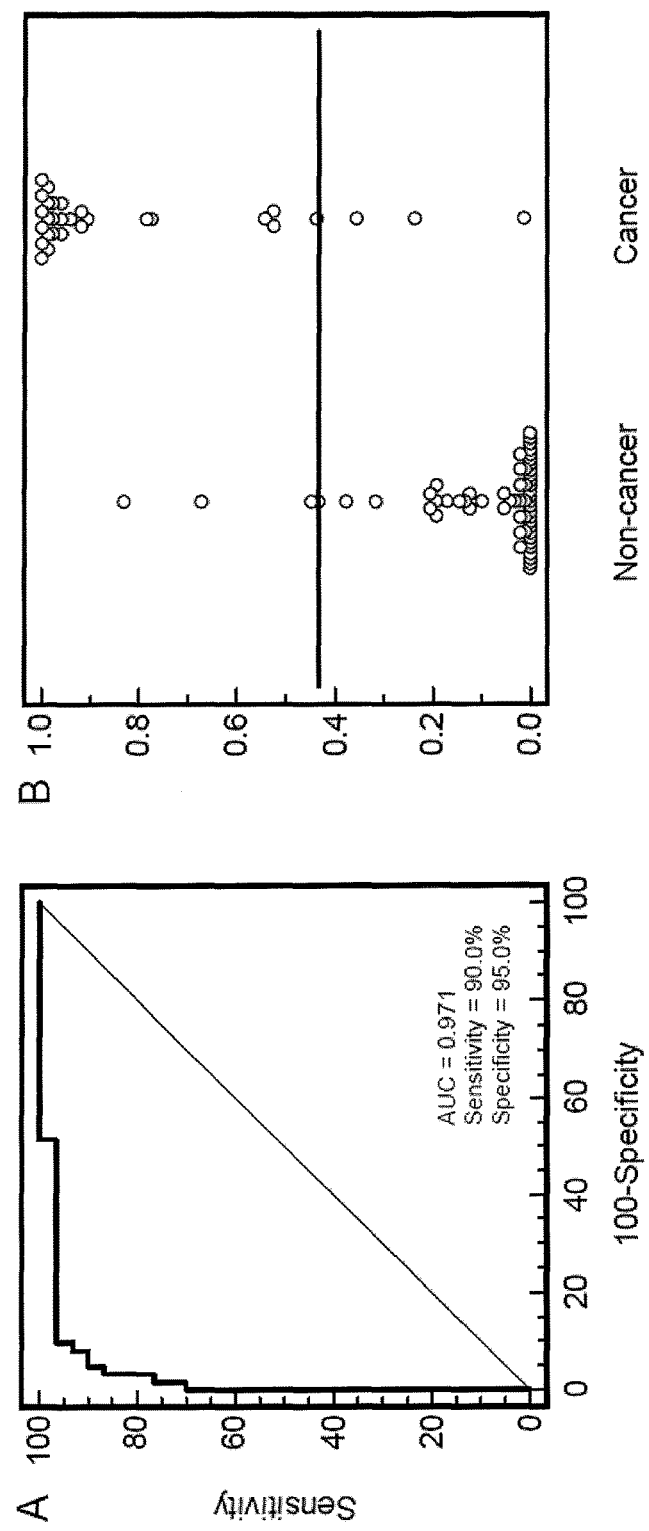
FIG. 2. ROC curve and interactive dot diagram for the logistic regression model. A. The logistic regression model using four biomarkers (KRAS, MBD3L2, ACRV1, and DPM1) yielded an AUC value of 0.971 (cutoff 0.433). B. Interactive dot diagram was based on the qPCR data of the non-cancer group (n=60) and cancer group (n=30).

To demonstrate the clinical utility of salivary mRNAs and bacteria biomarkers for pancreatic cancer discrimination, logistic regression models were built based on different combinations of biomarkers for three levels of clinical discrimination: pancreatic cancer vs. healthy control; pancreatic cancer vs. chronic pancreatitis and pancreatic cancer vs. non-cancer (healthy control+chronic pancreatitis) (FIG. 6). For pancreatic cancer vs. healthy control, the logistic regression model with the combination of four mRNA biomarkers (KRAS, MBD3L2, ACRV1 and CDKL3) yielded a ROC-plot AUC value of 0.973 (95% CI, 0.895 to 0.997; P<0.0001) with 93.3% sensitivity and 100% specificity in distinguishing pancreatic cancer patients from healthy control subjects. The logistic regression model with the combination of two bacterial biomarkers (*N. elongata* and *S. mitis*) yielded a ROC-plot AUC value of 0.895 (95% CI, 0.784 to 0.961; P<0.0001) with 96.4% sensitivity and 82.1% specificity in distinguishing pancreatic cancer patients from healthy subjects. For pancreatic cancer vs. chronic pancreatitis, the logistic regression model with the combination of three mRNA biomarkers (CDKL3, MBD3L2, KRAS) yielded a ROC-plot AUC value of 0.981 (95% CI, 0.907 to 0.997; P<0.0001) with 96.7% sensitivity and 96.7% specificity in distinguishing pancreatic cancer patients from chronic pancreatitis. Most importantly, for the discrimination of pancreatic cancer vs. non-cancer, the logistic regression model with the combination of four mRNA biomarkers (KRAS, MBD3L2, ACRV1 and DPM1) could differentiate pancreatic cancer patients from all non-cancer subjects, yielding a ROC-plot AUC value of 0.971 (95% CI, 0.911 to 0.994; P<0.0001). The four-biomarker logistic regression model provided the highest discriminatory power for differentiating pancreatic cancer from non-cancer subjects. Using a cutoff of 0.433, a sensitivity of 90.0% and a specificity of 95.0% was obtained for this four-biomarker logistic regression model (FIG. 2).

The effects of age and smoking history on the validated biomarkers were evaluated using linear regression models since these two factors were significantly different among the groups used for validation (Table 6). The regression models were used to determine if age and smoking had independent effects on the biomarkers which may have biased the diagnostic models. To avoid ecological correlation we performed these analyses separately within each group. We found that neither age nor smoking had effects on the markers more than we would expect by chance (only 2 out of 90 [2 covariates×15 markers×3 groups] tests were significant at α=0.05).

Discussion

The harnessing of valuable disease-specific biomarkers from body fluid samples such as saliva is imperative in current biomedical research. The salivary biomarkers that were identified here are highly discriminatory for the detection of early pancreatic cancer, with high sensitivity and specificity. Additionally, the methods presented here, a saliva-based diagnostic and early detection test for pancreatic cancer, are simple and non-invasive.

Understanding the profiles of molecular shifts in any particular cancer is extremely useful because it will become possible to correlate the cancer with its molecular signatures. Consistent with previous studies, our high-throughput analysis indicates that the mRNA in saliva supernatant is relatively stable and informative, and is a suitable source of biomarkers[16,17,29-32]. The consistency between different mRNA analysis methods (microarray and qPCR) demonstrates that the alteration of the salivary mRNA signatures between cancer group and control group can serve as biomarkers for early detection of pancreatic cancer. Out of the 12 validated mRNA biomarkers, several genes, e.g. MBD3L2, GLTSCR2 and TPT1, have been 33-41 linked to carcinogenesis[33-41]. Of particular interest is that KRAS, a frequently mutated molecular target in pancreatic cancer[42,43], is a discriminatory biomarker in saliva. It remains to be investigated whether the aberrant expressions of these genes are mediated by salivary glands or by other mechanisms. It has been shown that there is a disease-specific profile change in salivary mRNA biomarkers using the rodent models for systemic disease development[44].

The HOMIM profiling of microflora in the saliva pellet revealed that microbial composition shifts significantly between early pancreatic cancer and control subjects, providing informative signatures for biomarker discovery. A recent prospective study provided a pioneering link between oral health and the risk of pancreatic cancer[45]. However, it is unclear whether the variation in bacterial abundance is a derivational reflection of cancer onset due to the change of oral niches.

Bearing in mind that it is unlikely that a single biomarker will detect a specific cancer with high specificity and sensitivity, we used logistic regression to evaluate the combinations of biomarkers. The combination of multiple biomarkers increased the ROC-plot AUC values to much higher levels. It is particularly notable that the validated biomarkers can also discriminate early stage pancreatic cancer from chronic pancreatitis with high sensitivity and specificity, demonstrating that these salivary biomarkers are specific for the detection of early pancreatic cancer without the complication of chronic pancreatitis.

The determination of specific profiles of molecular changes in a specific cancer types is important because it is possible that the different cancers may have overlapping signatures. We have evaluated the specificity of the 12 validated mRNA biomarkers against other microarray discovery studies that have been performed in our laboratory on diverse cancers, including oral cancer (HG U133A)[17], breast cancer (HG U133 Plus 2.0), and lung cancer (HG U133 Plus 2.0) (unpublished data). With the exception of TK2 that showed significant variation in lung cancer, none of the other 11 mRNAs/transcripts were significantly altered in other cancer microarray studies (Table 5). In addition, all bacterial biomarkers validated in this study were also compared to another HOMIM profiling study using lung cancer saliva pellet (unpublished data). None were included in the list of significant altered species in the microflora profile of lung cancer. All these cross-disease comparisons clearly demonstrated that the validated mRNA biomarkers and bacterial biomarkers in saliva are specific for pancreatic cancer.

TABLE 1

| Discovery set number | Ethnicity | age | gender | smoking | drinking | diagnosis |
|---|---|---|---|---|---|---|
| Discovery sample set (12 PanCAN, 12 healthy control) | | | | | | |
| D-PanCAN-001 | caucasian | 75 | m | No | No | PC |
| D-PanCAN-002 | asian | 76 | f | No | No | PC |
| D-PanCAN-003 | caucasian | 60 | m | No | No | PC |
| D-PanCAN-004 | caucasian | 71 | f | No | No | PC |
| D-PanCAN-005 | caucasian | 65 | f | No | No | PC |
| D-PanCAN-006 | Hispanic | 83 | f | No | No | PC |
| D-PanCAN-007 | hispanic | 65 | m | No | Yes | PC |
| D-PanCAN-008 | caucasian | 68 | m | No | No | PC |
| D-PanCAN-009 | caucasian | 51 | m | No | No | PC |
| D-PanCAN-010 | caucasian | 81 | m | No | No | PC |
| D-PanCAN-011 | caucasian | 67 | m | No | No | PC |
| D-PanCAN-012 | caucasian | 71 | m | No | No | PC |
| D-Ctrl-001 | caucasian | 74 | m | No | No | Normal |
| D-Ctrl-002 | caucasian | 51 | f | No | No | Normal |
| D-Ctrl-003 | caucasian | 66 | m | No | No | Normal |
| D-Ctrl-004 | caucasian | 54 | f | No | No | Normal |
| D-Ctrl-005 | caucasian | 73 | m | No | No | Normal |
| D-Ctrl-006 | caucasian | 79 | m | No | No | Normal |
| D-Ctrl-007 | hispanic | 73 | f | No | No | Normal |
| D-Ctrl-008 | caucasian | 82 | m | No | No | Normal |
| D-Ctrl-009 | caucasian | 65 | m | No | No | Normal |
| D-Ctrl-010 | caucasian | 57 | m | No | No | Normal |
| D-Ctrl-011 | hispanic | 86 | m | No | No | Normal |
| D-Ctrl-012 | asian | 49 | f | No | No | Normal |
| Validation sample set (30 PanCAN, 30 healthy control, 30 Chronic pancreatitis) | | | | | | |
| V-PanCAN-001 | african american | 76 | f | No | No | PC |
| V-PanCAN-002 | hispanic | 74 | m | No | No | PC |
| V-PanCAN-003 | Asian | 73 | f | No | No | PC |
| V-PanCAN-004 | caucasian | 67 | m | Yes | No | PC |
| V-PanCAN-005 | caucasian | 57 | m | No | No | PC |
| V-PanCAN-006 | caucasian | 82 | m | No | No | PC |
| V-PanCAN-007 | caucasian | 75 | m | No | No | pc |
| V-PanCAN-008 | caucasian | 66 | m | No | No | pc |
| V-PanCAN-009 | caucasian | 53 | m | No | No | pc |
| V-PanCAN-010 | caucasian | 54 | m | Yes | No | pc |
| V-PanCAN-011 | caucasian | 90 | m | No | No | pc |
| V-PanCAN-012 | caucasian | 82 | m | No | No | pc |
| V-PanCAN-013 | asian | 66 | m | No | No | pc |
| V-PanCAN-014 | asian | 53 | f | No | No | pc |
| V-PanCAN-015 | caucasian | 72 | m | No | Yes | pc |
| V-PanCAN-016 | hispanic | 69 | f | No | No | pc |
| V-PanCAN-017 | asian | 82 | f | No | No | pc |
| V-PanCAN-018 | caucasian | 57 | f | Yes | No | pc |
| V-PanCAN-019 | caucasian | 79 | m | No | No | pc |
| V-PanCAN-020 | caucasian | 70 | f | No | No | pc |
| V-PanCAN-021 | caucasian | 79 | m | No | No | pc |
| V-PanCAN-022 | caucasian | 80 | f | Yes | No | pc |
| V-PanCAN-023 | hispanic | 78 | f | No | Yes | pc |
| V-PanCAN-024 | caucasian | 66 | m | Yes | No | pc |
| V-PanCAN-025 | caucasian | 61 | m | No | No | pc |
| V-PanCAN-026 | caucasian | 82 | m | No | No | pc |
| V-PanCAN-027 | caucasian | 56 | m | No | No | pc |
| V-PanCAN-028 | african american | 74 | f | No | No | pc |
| V-PanCAN-029 | hispanic | 75 | m | No | No | pc |
| V-PanCAN-030 | caucasian | 40 | f | No | No | pc |
| V-Ctrl-001 | african american | 73 | f | No | No | Normal |
| V-Ctrl-002 | caucasian | 59 | m | Yes | No | Normal |
| V-Ctrl-003 | Asian | 73 | f | No | No | Normal |
| V-Ctrl-004 | caucasian | 59 | m | No | No | Normal |
| V-Ctrl-005 | caucasian | 80 | m | No | Yes | Normal |
| V-Ctrl-006 | caucasian | 54 | m | Yes | No | Normal |
| V-Ctrl-007 | caucasian | 76 | m | No | No | Normal |
| V-Ctrl-008 | caucasian | 75 | m | No | No | Normal |
| V-Ctrl-009 | caucasian | 73 | f | No | No | Normal |
| V-Ctrl-010 | caucasian | 45 | f | No | No | Normal |
| V-Ctrl-011 | caucasian | 68 | m | No | No | Normal |
| V-Ctrl-012 | caucasian | 70 | m | No | No | Normal |
| V-Ctrl-013 | caucasian | 75 | m | No | No | Normal |
| V-Ctrl-014 | caucasian | 57 | m | No | No | Normal |
| V-Ctrl-015 | caucasian | 71 | m | No | Yes | Normal |
| V-Ctrl-016 | caucasian | 80 | f | No | No | Normal |
| V-Ctrl-017 | asian | 69 | f | No | No | Normal |
| V-Ctrl-018 | african american | 68 | f | No | No | Normal |
| V-Ctrl-019 | Asian | 69 | f | No | No | Normal |
| V-Ctrl-020 | caucasian | 51 | m | No | No | Normal |
| V-Ctrl-021 | caucasian | 59 | f | No | No | Normal |
| V-Ctrl-022 | hispanic | 70 | f | No | No | Normal |
| V-Ctrl-023 | hispanic | 49 | m | No | No | Normal |
| V-Ctrl-024 | hispanic | 75 | m | No | No | Normal |
| V-Ctrl-025 | caucasian | 56 | m | No | No | Normal |
| V-Ctrl-026 | caucasian | 59 | m | No | No | Normal |
| V-Ctrl-027 | caucasian | 49 | m | No | No | Normal |
| V-Ctrl-028 | asian | 60 | m | No | Yes | Normal |
| V-Ctrl-029 | caucasian | 63 | m | No | No | Normal |
| V-Ctrl-030 | hispanic | 63 | f | No | No | Normal |
| V-CP-001 | caucasian | 52 | m | Yes | No | CP |
| V-CP-002 | caucasian | 45 | m | No | No | CP |
| V-CP-003 | caucasian | 67 | m | Yes | No | CP |
| V-CP-004 | asian | 65 | m | No | No | CP |
| V-CP-005 | caucasian | 62 | m | No | No | CP |
| V-CP-006 | caucasian | 42 | m | Yes | No | CP |
| V-CP-007 | caucasian | 61 | m | Yes | No | CP |
| V-CP-008 | african american | 52 | f | Yes | No | CP |
| V-CP-009 | hispanic | 45 | f | No | No | CP |
| V-CP-010 | hispanic | 27 | m | No | Yes | CP |
| V-CP-011 | caucasian | 49 | m | No | No | CP |
| V-CP-012 | african american | 57 | f | No | No | CP |
| V-CP-013 | caucasian | 43 | m | No | No | CP |
| V-CP-014 | Asian | 63 | m | Yes | No | CP |
| V-CP-015 | caucasian | 51 | f | Yes | No | CP |
| V-CP-016 | caucasian | 59 | m | No | Yes | CP |
| V-CP-017 | caucasian | 49 | f | No | No | CP |
| V-CP-018 | caucasian | 52 | f | Yes | No | CP |
| V-CP-019 | caucasian | 62 | f | No | No | CP |
| V-CP-020 | hispanic | 72 | f | No | No | CP |
| V-CP-021 | caucasian | 48 | f | No | No | CP |
| V-CP-022 | asian | 35 | m | Yes | No | CP |
| V-CP-023 | caucasian | 72 | f | No | No | CP |
| V-CP-024 | hispanic | 70 | f | No | No | CP |
| V-CP-025 | caucasian | 54 | m | Yes | No | CP |
| V-CP-026 | caucasian | 51 | m | Yes | No | CP |
| V-CP-027 | caucasian | 47 | f | No | No | CP |
| V-CP-028 | asian | 64 | m | No | No | CP |
| V-CP-029 | caucasian | 54 | f | Yes | Yes | CP |
| V-CP-030 | caucasian | 59 | f | No | No | CP |

TABLE 2

Primers of 35 confirmed transcripts and GAPDH

| Gene symbol | Primer name | Primer sequences (5'-3') |
|---|---|---|
| ACRV1 | ACRV1-OF | GTCTTCGTGGAGAGGGAACCT (SEQ ID NO: 1) |
| | ACRV1-IF | GGGAACCTGCATCACTCAGAAT (SEQ ID NO: 2) |
| | ACRV1-IR | AGTTTTCCACCTTCAAAGATCTTCTT (SEQ ID NO: 3) |
| | ACRV1-OR | CACACCCTTGAACCATGAATTG (SEQ ID NO: 4) |
| CDC14B | CDC14B-OF | CTGCCCATTGTTTGGTTGC (SEQ ID NO: 5) |

TABLE 2-continued

Primers of 35 confirmed transcripts and GAPDH

| Gene symbol | Primer name | Primer sequences (5'-3') |
|---|---|---|
| | CDC14B-IF | GTTTGGTTGCCAGTCATACAAATTA (SEQ ID NO: 6) |
| | CDC14B-IR | ATTGCTGTTTCCAAGGGGAA (SEQ ID NO: 7) |
| | CDC14B-OR | TAAGCCGACATTATTTGGGATTG (SEQ ID NO: 8) |
| ASH2L | ASH2L-OF | CTGTCTCAAATGTTCTCCCAAAGAT (SEQ ID NO: 9) |
| | ASH2L-IF | CAAATGTTCTCCCAAAGATGCTAA (SEQ ID NO: 10) |
| | ASH2L-IR | CAGTCCTACCCAGCCTTTTAACTT (SEQ ID NO: 11) |
| | ASH2L-OR | GCAGTCTCCCGCAGTCCTAC (SEQ ID NO: 12) |
| STIM2 | STIM2-OF | GAAAGCCACGATGGACTTACAAG (SEQ ID NO: 13) |
| | STIM2-IF | TTAATGGACTCGTAAGCCAGCAT (SEQ ID NO: 14) |
| | STIM2-IR | AGAAGATGCTCTGGTAAACAAGAAATT (SEQ ID NO: 15) |
| | STIM2-OR | CTCTGTGGAAAGATAAGAAGATGCTCT (SEQ ID NO: 16) |
| GPR124 | GPR124-OF | TAGAGGATCTCATGACACCATACACA (SEQ ID NO: 17) |
| | GPR124-IF | CCCATCATTGCCTGTGAATG (SEQ ID NO: 18) |
| | GPR124-IR | CCCAGCAGTATCAACCCTCAG (SEQ ID NO: 19) |
| | GPR124-OR | CCCTCTGCTTGTGGAGTGGT (SEQ ID NO: 20) |
| LILRA2 | LILRA2-OF | GACAGATCTGATGATCCCAGGAG (SEQ ID NO: 21) |
| | LILRA2-IF | GGCTCTGGAGGACAATCTAGGA (SEQ ID NO: 22) |
| | LILRA2-IR | CTGTCTCTAGAAATGACCAGCATACAG (SEQ ID NO: 23) |
| | LILRA2-OR | TGATTGCTGTCTCTAGAAATGACCA (SEQ ID NO: 24) |
| ENG | ENG-OF | GCAAGAACAGTGGGCGTTG (SEQ ID NO: 25) |
| | ENG-IF | GAGCCTAGCTCCTGCCACAT (SEQ ID NO: 26) |
| | ENG-IR | AGGACAAGCAGCTTGGCTACTC (SEQ ID NO: 27) |
| | ENG-OR | CAGGACAAGCAGCTTGGCTAC (SEQ ID NO: 28) |
| RBM24 | RBM24-OF | GGTTAGCATTTTTATGGACTTTCTCC (SEQ ID NO: 29) |
| | RBM24-IF | GGACTTTCTCCATTATCACTGGATTT (SEQ ID NO: 30) |
| | RBM24-IR | TGCACAGGAGAGTCATGTCTACATT (SEQ ID NO: 31) |
| | RBM24-OR | GAATAAATAATTTGCACAGGAGAGTCAT (SEQ ID NO: 32) |
| LRRK1 | LRRK1-OF | GGGAAACTCAATCAGCAGGACT (SEQ ID NO: 33) |
| | LRRK1-IF | CAGGACTTCAGAAAGGGCCTT (SEQ ID NO: 34) |
| | LRRK1-IR | CTCCAGCTGCGTCCAAATTT (SEQ ID NO: 35) |
| | LRRK1-OR | AAACAAACAGGGCCTGTGCT (SEQ ID NO: 36) |
| DMXL2 | DMXL2-OF | GATGTATTTCCTTGGTTATGACCAAA (SEQ ID NO: 37) |
| | DMXL2-IF | GTTGAGATACTGAAACTAATGTCTGTGTGT (SEQ ID NO: 38) |
| | DMXL2-IR | TTAACATGATAAGACAATTTGCTGGTAA (SEQ ID NO: 39) |
| | DMXL2-OR | ACACAGGCATTGAACATTCTCATT (SEQ ID NO: 40) |
| DMD | DMD-OF | CCCAAATGCAAACAGTCTCTTCTATT (SEQ ID NO: 41) |
| | DMD-IF | GCAAACAGTCTCTTCTATTTCTTTCTTTTT (SEQ ID NO: 42) |
| | DMD-IR | GTGGCAACTGGACATCAGCTTAT (SEQ ID NO: 43) |
| | DMD-OR | AATTGTCAAGTGACGTGGGAAAGT (SEQ ID NO: 44) |
| MBD3L2 | MBD3L2-OF | GAGAAGGTTCAAGTCCACTGCATT (SEQ ID NO: 45) |
| | MBD3L2-IF | TGCATTTGGAGAGCGTCTTAAGTAT (SEQ ID NO: 46) |
| | MBD3L2-IR | CCAGAGATTCACTGGCCGTC (SEQ ID NO: 47) |
| | MBD3L2-OR | CTCAGCACCAGCTCTGTCCAG (SEQ ID NO: 48) |
| ITGA2B | ITGA2B-OF | CTTCCCACAGCCTCCTGTCA (SEQ ID NO: 49) |
| | ITGA2B-IF | AACCCTCTCAAGGTGGACTGG (SEQ ID NO: 50) |
| | ITGA2B-IR | CTGCGATCCCGCTTGTGAT (SEQ ID NO: 51) |
| | ITGA2B-OR | CAGGAAGATCTGTCTGCGATCC (SEQ ID NO: 52) |
| CDH4 | CDH4-OF | GATGATAATTCTGTTCTCTCCAAAGCA (SEQ ID NO: 53) |
| | CDH4-IF | GGGTAGTCTCAATTTCTGTCAGTGC (SEQ ID NO: 54) |
| | CDH4-IR | GAGATTCTGTGTTGATTCTTTTGGTG (SEQ ID NO: 55) |

TABLE 2-continued

Primers of 35 confirmed transcripts and GAPDH

| Gene symbol | Primer name | Primer sequences (5'-3') |
|---|---|---|
| | CDH4-OR | GGTCACGTGTGTCTGGGAGATT (SEQ ID NO: 56) |
| SAT1 | SAT1-OF | CTTGAATATCTTTCGATAAACAACAAGGT (SEQ ID NO: 57) |
| | SAT1-IF | GATAAACAACAAGGTGGTGTGATCTTAA (SEQ ID NO: 58) |
| | SAT1-IR | CACATTTAAATGACTCACGAGAATGAA (SEQ ID NO: 59) |
| | SAT1-OR | CAAACAGAAACTCTAAGTACCAGTGTGTAC (SEQ ID NO: 60) |
| FTHP1 | FTHP1-OF | CCCATAGCTGTGGGGTGACTT (SEQ ID NO: 61) |
| | FTHP1-IF | CAAGGCAGTGCATGCATGTT (SEQ ID NO: 62) |
| | FTHP1-IR | GGTACAAATCAAAAGAACTTAAGTGGATG (SEQ ID NO: 63) |
| | FTHP1-OR | TGAAGGAATGGTACAAATCAAAAGAAC (SEQ ID NO: 64) |
| TPT1 | TPT1-OF | GGATCTATCACCTGTCATCATAACTGG (SEQ ID NO: 65) |
| | TPT1-IF | ATCATAACTGGCTTCTGCTTGTCAT (SEQ ID NO: 66) |
| | TPT1-IR | GATGACATCAGTCCCATTTGTCTTAA (SEQ ID NO: 67) |
| | TPT1-OR | ATGAAGAGCTCAAGATGACATCAGTC (SEQ ID NO: 68) |
| FTH1 | FTH1-OF | CCCATTTGTGTGACTTCATTGAGA (SEQ ID NO: 69) |
| | FTH1-IF | CATTACCTGAATGAGCAGGTGAAA (SEQ ID NO: 70) |
| | FTH1-IR | GCAAGTTGGTCACGTGGTCA (SEQ ID NO: 71) |
| | FTH1-OR | GCTCCCATCTTGCGCAAGT (SEQ ID NO: 72) |
| SAT1 | SAT1-OF | TGGCAATCTCAGATGCAGTTTG (SEQ ID NO: 73) |
| | SAT1-IF | GGAGAGTCAGATCTTTCTCCTTGAATAT (SEQ ID NO: 74) |
| | SAT1-IR | TTAAGATCACACCACCTTGTTGTTTATC (SEQ ID NO: 75) |
| | SAT1-OR | TTCAAATATATTAAGATCACACCACCTTGT (SEQ ID NO: 76) |
| MARCKS | MARCKS-OF | CGGCAGAGTAAAAGAGCAAGCT (SEQ ID NO: 77) |
| | MARCKS-IF | GCAAGCTTTTGTGAGATAATCGAA (SEQ ID NO: 78) |
| | MARCKS-IR | GGCACCACTCCAACAAACAAA (SEQ ID NO: 79) |
| | MARCKS-OR | CCTGGTTGTAGACAAGTTCTCCAA (SEQ ID NO: 80) |
| PNPLA8 | PNPLA8-OF | TGGCCAGATGTGCCGTTAG (SEQ ID NO: 81) |
| | PNPLA8-IF | AGATGTGCCGTTAGAGTGCATAGTAT (SEQ ID NO: 82) |
| | PNPLA8-IR | CCGTGTTTCTCACATCACTCTCAT (SEQ ID NO: 83) |
| | PNPLA8-OR | TCAAGCTTGTGTATGTTACCGTGTT (SEQ ID NO: 84) |
| DPM1 | DPM1-OF | GAGATGATTGTTCGGGCAAGA (SEQ ID NO: 85) |
| | DPM1-IF | TTCGGGCAAGACAGTTGAATTATA (SEQ ID NO: 86) |
| | DPM1-IR | TCACCATAAACACGATCCACAAA (SEQ ID NO: 87) |
| | DPM1-OR | TTCATTTCCTCCCAACTTGGAT (SEQ ID NO: 88) |
| CD7 | CD7-OF | TGGCGGTGATCTCCTTCCT (SEQ ID NO: 89) |
| | CD7-IF | GCTGGCGAGGACACAGATAAA (SEQ ID NO: 90) |
| | CD7-IR | ATGCCGCCGAATTCTTATCC (SEQ ID NO: 91) |
| | CD7-OR | TGTGCGACATGTCCTCGTACA (SEQ ID NO: 92) |
| GPR37 | GPR37-OF | GAAGTGGCTGCTGGAGGACTT (SEQ ID NO: 93) |
| | GPR37-IF | CCTGCAAGATCGTGCCCTATA (SEQ ID NO: 94) |
| | GPR37-IR | TGCACAGAGCACATAAGGTGAA (SEQ ID NO: 95) |
| | GPR37-OR | CACGGAAGCGGTCTATGCA (SEQ ID NO: 96) |
| PCSK6 | PCSK6-OF | ACCTCCTGCATCACCAACCA (SEQ ID NO: 97) |
| | PCSK6-IF | AGCAACGCTGACGAGACATTC (SEQ ID NO: 98) |
| | PCSK6-IR | CACAGCCGGTTGGACTTCA (SEQ ID NO: 99) |
| | PCSK6-OR | CGGCAGCAGAACTGAATGAA (SEQ ID NO: 100) |
| TK2 | TK2-OF | GCCCCTGTTCTGGTGATTGA (SEQ ID NO: 101) |
| | TK2-IF | CCACCACATGGAGAGGATGTTA (SEQ ID NO: 102) |
| | TK2-IR | TCCGATTCTCTGGAGTTAATATTCG (SEQ ID NO: 103) |
| | TK2-OR | AGCCATAGACCTTTTGCCTCCTA (SEQ ID NO: 104) |
| TTBK2 | TTBK2-OF | TAGAAGCCAGGCTACGCAGATATA (SEQ ID NO: 105) |

TABLE 2-continued

Primers of 35 confirmed transcripts and GAPDH

| Gene symbol | Primer name | Primer sequences (5'-3') |
|---|---|---|
|  | TTBK2-IF | CCTGGCCCAAATTCTTCAAA (SEQ ID NO: 106) |
|  | TTBK2-IR | CCTGGACTCTTGCACTGAGTAGTG (SEQ ID NO: 107) |
|  | TTBK2-OR | AGATCCTGGACTCTTGCACTGAGT (SEQ ID NO: 108) |
| GLTSCR2 | GLTSCR2-OF | GACCGGTTCAAGAGCTTCCA (SEQ ID NO: 109) |
|  | GLTSCR2-IF | TTCCAGAGGAGGAATATGATCGA (SEQ ID NO: 110) |
|  | GLTSCR2-IR | TTCTCCACCAGCTTCACCTTGTA (SEQ ID NO: 111) |
|  | GLTSCR2-OR | TGATGGCAGCTACAACTGGATCT (SEQ ID NO: 112) |
| CDKL3 | CDKL3-OF | TCAGTTTTGGGAGAGGAAATAGAAA (SEQ ID NO: 113) |
|  | CDKL3-IF | TAGAAAAAGAGAAAAAGCCCAAGGA (SEQ ID NO: 114) |
|  | CDKL3-IR | TCTCCTCTTCCTCCTTTGACTTTAAT (SEQ ID NO: 115) |
|  | CDKL3-OR | TCCACCTTCATACTCTTTCTTTTTG (SEQ ID NO: 116) |
| ZSCAN16 | ZSCAN16-OF | CTCCTCAGCATCCTAAGTCCAAA (SEQ ID NO: 117) |
|  | ZSCAN16-IF | GGGCAGATCAGAATGGCAA (SEQ ID NO: 118) |
|  | ZSCAN16-IR | CCACATTCATCACATTTATATCGTCTT (SEQ ID NO: 119) |
|  | ZSCAN16-OR | GCTATGACTGAAACTTTTCCCACAT (SEQ ID NO: 120) |
| S100P | S100P-OF | GCACGCAGACCCTGACCA (SEQ ID NO: 121) |
|  | S100P-IF | GCTGATGGAGAAGGAGCTACCA (SEQ ID NO: 122) |
|  | S100P-IR | TTGAGCAATTTATCCACGGCAT (SEQ ID NO: 123) |
|  | S100P-OR | CGTCCAGGTCCTTGAGCAATT (SEQ ID NO: 124) |
| KRAS | KRAS-OF | AGACACAAAACAGGCTCAGGACTT (SEQ ID NO: 125) |
|  | KRAS-IF | CAGGCTCAGGACTTAGCAAGAAG (SEQ ID NO: 126) |
|  | KRAS-IR | CACCCTGTCTTGTCTTTGCTGAT (SEQ ID NO: 127) |
|  | KRAS-OR | GGCATCATCAACACCCTGTCT (SEQ ID NO: 128) |
| UTF1 | UTF1-OF | CCCCCGTCGCTGAACAC (SEQ ID NO: 129) |
|  | UTF1-IF | GGCGACATCGCGAACATC (SEQ ID NO: 130) |
|  | UTF1-IR | GCTCCACGTGCTGGTTCAA (SEQ ID NO: 131) |
|  | UTF1-OR | CGGCCAGGGACACTGTCT (SEQ ID NO: 132) |
| ZMIZ2 | ZMIZ2-OF | GGACCTGCTCCCGGAACT (SEQ ID NO: 133) |
|  | ZMIZ2-IF | GGAACTGACCAACCCTGATGAG (SEQ ID NO: 134) |
|  | ZMIZ2-IR | CAGGTCGTCATTGTTGTTCGTAG (SEQ ID NO: 135) |
|  | ZMIZ2-OR | AACAGAGAAAGCAGGTCGTCATT (SEQ ID NO: 136) |
| DDX3X | DDX3X-OF | GAGGTGGCTATGGAGGCTTTTA (SEQ ID NO: 137) |
|  | DDX3X-IF | CAACAGTGATGGATATGGAGGAAA (SEQ ID NO: 138) |
|  | DDX3X-IR | GCTCAGTTACCCCACCAGTCAA (SEQ ID NO: 139) |
|  | DDX3X-OR | TGTTTGGCAGGGTGACCTACT (SEQ ID NO: 140) |
| CABLES1 | CABLES1-OF | GTCCTCAGCCTTGTGGTAGCA (SEQ ID NO: 141) |
|  | CABLES1-IF | TGGTAGCACAAATGAATGCAGTAA (SEQ ID NO: 142) |
|  | CABLES1-IR | GCAGTATTCTGTGAACGCTGGTA (SEQ ID NO: 143) |
|  | CABLES1-OR | CAAGATTTGAGGTTCAGTGCAGTATT (SEQ ID NO: 144) |
| GAPDH | GAPDH-OF | CATTGCCCTCAACGACCACTT (SEQ ID NO: 145) |
|  | GAPDH-IF | ACCACTTTGTCAAGCTCATTTCCT (SEQ ID NO: 146) |
|  | GAPDH-IR | CACCCTGTTGCTGTAGCCAAAT (SEQ ID NO: 147) |
|  | GAPDH-OR | ATGTGGGCCATGAGGTCCA (SEQ ID NO: 148) |

OF = Outer forward, IF = Inner forward, IR = Inner reverse, OR = Outer reverse

TABLE 3 qPCR primers of 6 confirmed bacterial species

| Strain | 16S rRNA primer sequences (5'-3') |
|---|---|
| Atopobium parvulum | F: CGAATACTTCGAGACTTCCGCA (SEQ ID NO: 149) |
|  | R: CAATCTGGCTGGTCGGTCTC (SEQ ID NO: 150) |
| Granulicatella adiacens | F: CAAGCTTCTGCTGATGGATGGA (SEQ ID NO: 151) |

TABLE 3-continued qPCR primers of 6 confirmed bacterial species

| Strain | 16S rRNA primer sequences (5'-3') |
|---|---|
| | R: CTCAGGTCGGCTATGCATCAC (SEQ ID NO: 152) |
| Neisseria elongata | F: CATGCCGCGTGTCTGAAGAA (SEQ ID NO: 153) |
| | R: CCGTCAGCAGAAACGGGTATT (SEQ ID NO: 154) |
| Prevotella nigrescens | F: GACGGCATCCGATATGAAACA (SEQ ID NO: 155) |
| | R: TGCACGCTACTTGGCTGGT (SEQ ID NO: 156) |
| Streptococcus australis | F: AGAACGCTGAAGGAAGGAGCTT (SEQ ID NO: 157) |
| | R: CAATAGTTATCCCCCGCTACCA (SEQ ID NO: 158) |
| Streptococcus mitis | F: CCGCATAATAGCAGTTRTTGCA (SEQ ID NO: 159) |
| | R: ACAACGCAGGTCCATCTGGTA (SEQ ID NO: 160) |

TABLE 4

Salivary mRNA up and down-regulated in pancreatic cancer confirmed by microarray and qPCR

| Gene symbol | Gene name | GenBank accession no. | Locus | Gene functions |
|---|---|---|---|---|
| *up-regulated genes* | | | | |
| ACRV1 | acrosomal vesicle protein 1 | NM_001612 | 11q23-q24 | multicellular organismal development |
| CDC14B | CDC14 cell division cycle 14 homolog B | NM_003671 | 9q22.33 | protein amino acid dephosphorylation; cell division |
| ASH2L | ash2-like | NM_004674 | 8p11.2 | regulation of transcription |
| STIM2 | stromal interaction molecule 2 | NM_020860 | 4p15.2 | calcium ion binding and transport |
| GPR124 | G protein-coupled receptor 124 | NM_032777 | 8p12 | G-protein coupled receptor protein signaling pathway; neuropeptide signaling pathway |
| LILRA2 | leukocyte immunoglobulin-like receptor, subfamily A, member 2 | NM_006866 | 19q13.4 | defense response; immune response; signal transduction |
| ENG | endoglin | NM_000118 | 9q33-q34.1 | transport; cell adhesion; blood circulation; organ morphogenesis |
| RBM24 | RNA binding motif protein 24 | NM_153020 | 6p22.3 | type I hypersensitivity |
| LRRK1 | leucine-rich repeat kinase 1 | NM_024652 | 15q26.3 | protein amino acid phosphorylation; small GTPase mediated signal transduction |
| DMXL2 | Dmx-like 2 | NM_015263 | 15q21.2 | translational initiation |
| ZSCAN16 | zinc finger and SCAN domain containing 16 | NM_025231 | 6p22.1 | regulation of transcription, DNA-dependent |
| MBD3L2 | methyl-CpG binding domain protein 3-like 2 | NM_144614 | 19p13.2 | oppose MBD2-MeCP1-mediated methylation silencing |
| GPX3 | glutathione peroxidase 3 | NM_002084 | 5q23 | glutathione metabolic process; response to oxidative stress |
| ITGA2B | integrin, alpha 2b | NM_000419 | 17q21.32 | cell adhesion; integrin-mediated signaling pathway; platelet activation |
| CDH4 | cadherin 4 | NM_001794 | 20q13.3 | homophilic cell adhesion; positive regulation of axon extension |
| S100P | S100 calcium binding protein P | NM_005980 | 4p16 | endothelial cell migration |
| FTHP1 | ferritin, heavy polypeptide pseudogene 1 | NG_005639 | 6p21.3-p12 | |
| ZMIZ2 | zinc finger, MIZ-type containing 2 | NM_031449 | 7p13 | regulation of transcription, DNA-dependent |
| DDX3X | DEAD (Asp-Glu-Ala-Asp; SEQ ID NO: 161) box polypeptide 3, X-linked | NM_001356 | Xp11.3-p11.23 | embryogenesis; spermatogenesis; cellular growth and division |
| UTF1 | undifferentiated embryonic cell transcription factor 1 | NM_003577 | 10q26 | regulation of transcription, DNA-dependent |
| KRAS | v-Ki-ras2 Kirsten rat sarcoma viral oncogene homolog | NM_004985 | 12p12.1 | small GTPase mediated signal transduction; Ras protein signal transduction |
| DMD | dystrophin | NM_000109 | Xp21.2 | cytoskeletal anchoring at plasma membrane; peptide biosynthetic process |
| CABLES1 | Cdk5 and Abl enzyme substrate 1 | NM_001100619 | 18q11.2 | regulation of cell division; regulation of cell cycle |
| *Down-regulated genes* | | | | |
| TPT1 | tumor protein, translationally-controlled 1 | NM_003295 | 13q12-q14 | cellular calcium ion homeostasis; anti-apoptosis regulation of apoptosis |
| MARCKS | myristoylated alanine-rich protein kinase C substrate | NM_002356 | 6q22.2 | cell motility; phagocytosis; membrane trafficking; mitogenesis |
| SAT1 | spermidine/spermine N1-acetyltransferase 1 | NM_002970 | Xp22.1 | metabolic process |
| PNPLA8 | patatin-like phospholipase domain containing 8 | NM_015723 | 7q31 | lipid metabolic process; modulates cellular growth programs; inflammation; ion channel function |
| DPM1 | dolichyl-phosphate mannosyltransferase polypeptide 1 | NM_003859 | 20q13.13 | GPI anchor biosynthetic process; protein amino acid mannosylation |
| CD7 | CD7 molecule | NM_006137 | 17q25.2-q25.3 | immune response; tyrosine kinase signaling pathway; T cell activation |

TABLE 4-continued

Salivary mRNA up and down-regulated in pancreatic cancer confirmed by microarray and qPCR

| Gene symbol | Gene name | GenBank accession no. | Locus | Gene functions |
|---|---|---|---|---|
| PCSK6 | proprotein convertase subtilisin/kexin type 6 | NM_138319 | 15q26.3 | tumor progression; proteolysis; regulation of BMP signaling pathway |
| TK2 | thymidine kinase 2 | NM_004614 | 16q22-q23.1 | nucleotide and nucleic acid metabolic process; DNA replication |
| FTH1 | ferritin, heavy polypeptide 1 | NM_002032 | 11q13 | iron ion transport, immune response, negative regulation of cell proliferation, oxidation reduction |
| TUBA1A | tubulin, alpha 1b | NM_006082 | 12q13.12 | microtubule-based process, protein polymerization |
| GLTSCR2 | glioma tumor suppressor candidate region gene 2 | NM_015710 | 19q13.3 | tumor suppressive activity |
| CDKL3 | cyclin-dependent kinase-like 3 | NM_016508 | 5q31 | protein modification process; protein amino acid phosphorylation |

The human Genome U133 Plus 2.0 microarrays were used to identify the difference in RNA expression patterns in saliva from 12 pancreatic cancer patients and 12 healthy controls. Using a criteria of a change in regulation >4-fold in all 12 pancreatic cancer saliva specimens and a cutoff of p-value <0.01 in microarray study we identified 49 up-regulated and 21 down-regulated transcripts. These transcripts were subjected to qPCR verification. Using a cutoff of p-value <0.05 in the qPCR verification study, we identified 35 mRNAs, showing significant up-regulation (23 mRNAs) and significant down-regulation (12 mRNAs) in pancreatic cancer saliva.

TABLE 5

Cross-disease comparison of microarray profiles of 12 validated mRNA biomarkers

| Gene symbol | Pancreatic cancer | Oral cancer | Lung cancer | Breast cancer |
|---|---|---|---|---|
| MBD3L2 | 0.011 | 0.391 | 0.770 | 0.419 |
| KRAS | <0.001 | 0.248 | 0.346 | 0.906 |
| STIM2 | 0.013 | 0.160 | 0.479 | 0.963 |
| DMXL2 | 0.009 | 0.869 | 0.056 | 0.226 |
| ACRV1 | 0.004 | 0.946 | 0.304 | 0.397 |
| DMD | 0.008 | 0.633 | 0.979 | 0.558 |
| CABLES1 | 0.002 | 0.574 | 0.096 | 0.473 |
| TK2 | 0.014 | 0.966 | 0.007 | 0.311 |
| GLTSCR2 | 0.006 | 0.417 | 0.336 | 0.073 |
| CDKL3 | <0.001 | 0.107 | 0.227 | 0.190 |
| TPT1 | 0.007 | 0.213 | 0.331 | 0.422 |
| DPM1 | 0.005 | 0.135 | 0.082 | 0.428 |

Cancer specificity of the twelve validated mRNA biomarkers were evaluated across different microarray discovery studies that has been performed in our laboratory on diverse cancers, including pancreatic cancer (HG U133 Plus 2.0), oral cancer (HG U133A), breast cancer (HG U133 Plus 2.0) and lung cancer (HG U133 Plus 2.0). T-test p-values were calculated for each transcript between cancers and healthy controls in different microarray studies. Except TK2 that also showed significant variation in lung cancer microarray study (P < 0.05), the rest mRNAs/transcripts that showed significant variations in pancreatic cancer study were not significantly altered in other cancer microarray studies.

TABLE 6

Effect of age and smoking on the validated biomarkers

| Biomarker | Pancreatic cancer | | Healthy control | | Chronic pancreatitis | |
|---|---|---|---|---|---|---|
| | age | smoking | age | smoking | age | smoking |
| ACRV1 | 0.308 | 0.228 | 0.899 | 0.187 | 0.909 | 0.372 |
| STIM2 | 0.628 | 0.684 | 0.352 | 0.669 | 0.855 | 0.130 |
| DMXL2 | 0.674 | 0.621 | 0.158 | 0.869 | 0.226 | 0.264 |
| CABLES1 | 0.398 | 0.370 | 0.489 | 0.154 | 0.829 | 0.314 |
| DMD | 0.599 | 0.540 | 0.281 | 0.097 | 0.663 | 0.234 |
| MBD3L2 | 0.535 | 0.201 | 0.366 | 0.078 | 0.396 | 0.601 |
| DPM1 | 0.550 | 0.617 | 0.345 | 0.177 | 0.729 | 0.732 |
| TK2 | 0.977 | 0.673 | 0.721 | 0.125 | 0.705 | 0.946 |
| GLTSCR2 | 0.153 | 0.199 | 0.687 | 0.361 | 0.883 | 0.207 |
| CDKL3 | 0.507 | 0.936 | 0.811 | 0.182 | 0.712 | 0.538 |
| TPT1 | 0.441 | 0.442 | 0.394 | 0.206 | 0.728 | 0.719 |
| KRAS | 0.461 | 0.380 | 0.776 | 0.880 | 0.845 | 0.820 |
| G. adiacens | 0.306 | 0.509 | 0.087 | 0.143 | 0.370 | 0.194 |
| N. elongata | 0.987 | 0.053 | 0.280 | 0.678 | 0.306 | 0.030 |
| S. mitis | 0.584 | 0.042 | 0.433 | 0.974 | 0.779 | 0.217 |

Effect of age and smoking history was calculated for the validated biomarkers. The effect was considered significant if p-value <0.05 (shown in bold). Gene names are listed in Table A4. We further evaluated the effect of these two factors on the model building (N. elongate and S. mitis). Neither of them contributes significantly to the models using microbial biomarkers after discounting the group difference.

1. Canto M I, Goggins M, Hruban R H, et al: Screening for early pancreatic neoplasia in high-risk individuals: a prospective controlled study. Clin Gastroenterol Hepatol 4:766-81; quiz 665, 2006.
2. Canto M I, Goggins M, Yeo C J, et al: Screening for pancreatic neoplasia in high-risk individuals: an EUS-based approach. Clin Gastroenterol Hepatol 2:606-21, 2004.
3. Rulyak S J, Kimmey M B, Veenstra D L, et al: Cost-effectiveness of pancreatic cancer screening in familial pancreatic cancer kindreds. Gastrointest Endosc 57:23-9, 2003.
4. Farrell J J, van Rijnsoever M, Elsaleh H: Early detection markers in Pancreas Cancer. Cancer Biomark 1:157-75, 2005.
5. Koopmann J, Rosenzweig C N, Zhang Z, et al: Serum markers in patients with resectable pancreatic adenocarcinoma: macrophage inhibitory cytokine 1 versus CA19-9. Clin Cancer Res 12:442-6, 2006.
6. Koopmann J, Zhang Z, White N, et al: Serum diagnosis of pancreatic adenocarcinoma using surface-enhanced laser desorption and ionization mass spectrometry. Clin Cancer Res 10:860-8, 2004.
7. Rogers C D, Fukushima N, Sato N, et al: Differentiating pancreatic lesions by microarray and QPCR analysis of pancreatic juice RNAs. Cancer Biol Ther 5:1383-9, 2006.
8. Whitcomb D C: Inflammation and Cancer V. Chronic pancreatitis and pancreatic cancer. Am J Physiol Gastrointest Liver Physiol 287:G315-9, 2004.
9. Goggins M, Canto M, Hruban R: Can we screen high-risk individuals to detect early pancreatic carcinoma? J Surg Oncol 74:243-8, 2000.

10. Locker G Y, Hamilton S, Harris J, et al: ASCO 2006 update of recommendations for the use of tumor markers in gastrointestinal cancer. J Clin Oncol 24:5313-27, 2006.
11. Pleskow D K, Berger H J, Gyves J, et al: Evaluation of a serologic marker, CA19-9, in the diagnosis of pancreatic cancer. Ann Intern Med 110:704-9, 1989.
12. Ballantyne J: Validity of messenger RNA expression analyses of human saliva. Clin Cancer Res 13:1350; author reply 1351, 2007.
13. Nussbaumer C, Gharehbaghi-Schnell E, Korschineck I: Messenger RNA profiling: a novel method for body fluid identification by real-time PCR. Forensic Sci Int 157:181-6, 2006.
14. Zubakov D, Hanekamp E, Kokshoorn M, et al: Stable RNA markers for identification of blood and saliva stains revealed from whole genome expression analysis of time-wise degraded samples. Int J Legal Med 122:135-42, 2008.
15. Hu S, Arellano M, Boontheung P, et al: Salivary proteomics for oral cancer biomarker discovery. Clin Cancer Res 14:6246-52, 2008.
16. Hu S, Wang J, Meijer J, et al: Salivary proteomic and genomic biomarkers for primary Sjogren's syndrome. Arthritis Rheum 56:3588-600, 2007.
17. Li Li Y, St John M A, Zhou X, et al: Salivary transcriptome diagnostics for oral cancer detection. Clin Cancer Res 10:8442-50, 2004.
18. Mager D L, Haffajee A D, Devlin P M, et al: The salivary microbiota as a diagnostic indicator of oral cancer: a descriptive, non-randomized study of cancer-free and oral squamous cell carcinoma subjects. J Transl Med 3:27, 2005.
19. Bigler L R, Streckfus C F, Copeland L, et al: The potential use of saliva to detect recurrence of disease in women with breast carcinoma. J Oral Pathol Med 31:421-31, 2002.
20. Goldenberg R L, Culhane J F: Preterm birth and periodontal disease. N Engl J Med 355:1925-7, 2006.
21. Streckfus C F, Mayorga-Wark O, Arreola D, et al: Breast cancer related proteins are present in saliva and are modulated secondary to ductal carcinoma in situ of the breast. Cancer Invest 26:159-67, 2008.
22. Streckfus C, Bigler L, Dellinger T, et al: The presence of soluble c-erbB-2 in saliva and serum among women with breast carcinoma: a preliminary study. Clin Cancer Res 6:2363-70, 2000.
23. Denny P, Hagen F K, Hardt M, et al: The proteomes of human parotid and submandibular/sublingual gland salivas collected as the ductal secretions. J Proteome Res 7:1994-2006, 2008.
24. Preza D, Olsen I, Willumsen T, et al: Microarray analysis of the microflora of root caries in elderly. Eur J Clin Microbiol Infect Dis, 2008.
25. Hu Z, Zimmermann B G, Zhou H, et al: Exon-level expression profiling: a comprehensive transcriptome analysis of oral fluids. Clin Chem 54:824-32, 2008.
26. Paster B J, Boches S K, Galvin J L, et al: Bacterial diversity in human subgingival plaque. J Bacteriol 183:3770-83, 2001.
27. Hanley J A, McNeil B J: The meaning and use of the area under a receiver operating characteristic (ROC) curve. Radiology 143:29-36, 1982.
28. Zweig M H, Campbell G: Receiver-operating characteristic (ROC) plots: a fundamental evaluation tool in clinical medicine. Clin Chem 39:561-77, 1993.
29. Li Y, Zhou X, St John M A, et al: RNA profiling of cell-free saliva using microarray technology. J Dent Res 83:199-203, 2004.
30. Park N J, Li Y, Yu T, et al: Characterization of RNA in saliva. Clin Chem 52:988-94, 2006.
31. Park N J, Yu T, Nabili V, et al: RNAprotect saliva: An optimal room-temperature stabilization reagent for the salivary transcriptome. Clin Chem 52:2303-4, 2006.
32. Park N J, Zhou X, Yu T, et al: Characterization of salivary RNA by cDNA library analysis. Arch Oral Biol 52:30-5, 2007.
33. Smith J S, Tachibana I, Pohl U, et al: A transcript map of the chromosome 19q-arm glioma tumor suppressor region. Genomics 64:44-50, 2000.
34. Kim Y J, Cho Y E, Kim Y W, et al: Suppression of putative tumour suppressor gene GLTSCR2 expression in human glioblastomas. J Pathol 216:218-24, 2008.
35. Okahara F, Ikawa H, Kanaho Y, et al: Regulation of PTEN phosphorylation and stability by a tumor suppressor candidate protein. J Biol Chem 279:45300-3, 2004.
36. Okahara F, Itoh K, Nakagawara A, et al: Critical role of PICT-1, a tumor suppressor candidate, in phosphatidylinositol 3,4,5-trisphosphate signals and tumorigenic transformation. Mol Biol Cell 17:4888-95, 2006.
37. Yim J H, Kim Y J, Ko J H, et al: The putative tumor suppressor gene GLTSCR2 induces PTEN-modulated cell death. Cell Death Differ 14:1872-9, 2007.
38. Arcuri F, Papa S, Carducci A, et al: Translationally controlled tumor protein (TCTP) in the human prostate and prostate cancer cells: expression, distribution, and calcium binding activity. Prostate 60:130-40, 2004.
39. Chung S, Kim M, Choi W, et al: Expression of translationally controlled tumor protein mRNA in human colon cancer. Cancer Lett 156:185-90, 2000.
40. Zhu W L, Cheng H X, Han N, et al: Messenger RNA expression of translationally controlled tumor protein (TCTP) in liver regeneration and cancer. Anticancer Res 28:1575-80, 2008.
41. Li Y, Elashoff D, Oh M, et al: Serum circulating human mRNA profiling and its utility for oral cancer detection. J Clin Oncol 24:1754-60, 2006.
42. Mulcahy H E, Lyautey J, Lederrey C, et al: A prospective study of K-ras mutations in the plasma of pancreatic cancer patients. Clin Cancer Res 4:271-5, 1998.
43. Pellegata N S, Sessa F, Renault B, et al: K-ras and p53 gene mutations in pancreatic cancer: ductal and nonductal tumors progress through different genetic lesions. Cancer Res 54:1556-60, 1994.
44. Kai Gao, Hui Zhou, Lei Zhang, et al: Systemic disease-induced salivary biomarker profiles in mouse models of melanoma and non-small cell lung cancer Los Angeles, UCLA Denal Research Institute, 2008.
45. Michaud D S, Joshipura K, Giovannucci E, et al: A prospective study of periodontal disease and pancreatic cancer in US male health professionals. J Natl Cancer Inst 99:171-5, 2007.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for distinguishing subjects with pancreatic cancer from those without pancreatic cancer, the method comprising:
   a) analyzing a saliva sample from a test subject with an assay that specifically detects at least four nucleic acid or polypeptide markers in the saliva sample, wherein at least four biomarkers are selected from the group consisting of MBD3L2, KRAS, ACRV1, CDKL3, and DPM1,
   b) detecting a change in the level of the at least four biomarkers selected from the group consisting of an increase in the level of MBD3L2, an increase in the level of KRAS, an increase in the level of ACRV1, a decrease in the level of CDKL3 and a decrease in the level of DPM1 relative to a control, thereby
   c) detecting the presence of pancreatic cancer in the test subject, and effectuating a pancreatic cancer treatment regimen on the test subject.

2. The method of claim 1, wherein the combination of markers is KRAS, MBD3L2, ACRV1, and DPM1, and wherein higher levels of KRAS, MBD3L2, and ACRV1, and a lower level of DPM1 relative to a control distinguishes the test subject from those subjects without pancreatic cancer and all of these markers are detected.

3. The method of claim 1, wherein those subjects with pancreatic cancer are distinguished from those subjects without pancreatic cancer but with chronic pancreatitis, the method comprising detecting a level of a combination of markers wherein the markers are MBD3L2, KRAS, STIM2, ACRV1, DMD, CABLES1, TK2, GLTSCR2, and CDKL3.

4. The method of claim 1, wherein the combination of markers is KRAS, MBD3L2 ACRV1 and CDKL3 and wherein higher levels of KRAS ACRV1 and MBD3L2 and a lower level of CDKL3 relative to a control distinguishes the test subject from those subjects without pancreatic cancer and all of these markers are detected.

5. The method of claim 4, further comprising the detection of at least one additional biomarker selected from the group consisting of STIM2, DMD, CABLES1, TK2, GLTSCR2 and DPM1.

6. A method comprising the steps of: obtaining a saliva sample from a test subject, detecting in the saliva sample a change in the level of at least four nucleic acid or polypeptide markers selected from the group consisting of an increase in the level of MBD3L2, an increase in the level of KRAS, an increase in the level of ACRV1, a decrease in the level of CDKL3, and a decrease in the level of DPM1 relative to a control, thereby detecting the presence of pancreatic cancer in the test subject, and effectuating a pancreatic cancer treatment regimen on the test subject.

7. A method of treating pancreatic cancer comprising administering a pancreatic cancer treatment regimen to a subject who has been identified as having a change in the level of at least four nucleic acid or polypeptide markers in a saliva sample of the subject, wherein the change in the level of at least four nucleic acid or polypeptide markers are selected from the group consisting of an increase in the level of MBD3L2, an increase in the level of KRAS, an increase in the level of ACRV1, a decrease in the level of CDKL3, and a decrease in the level of DPM1 relative to a control.

* * * * *

SEQUENCE LISTING

<160> NUMBER OF SEQ ID NOS: 161

<210> SEQ ID NO 1
<211> LENGTH: 21
<212> TYPE: DNA
<213> ORGANISM: Artificial Sequence
<220> FEATURE:
<223> OTHER INFORMATION: synthetic salivary transcriptome biomarker
      outer forward primer ACRV1-OF

<400> SEQUENCE: 1
gtcttcgtgg agagggaacc t                                              21

<210> SEQ ID NO 2
<211> LENGTH: 22
<212> TYPE: DNA
<213> ORGANISM: Artificial Sequence
<220> FEATURE:
<223> OTHER INFORMATION: synthetic salivary transcriptome biomarker
      inner forward primer ACRV1-IF

<400> SEQUENCE: 2
gggaacctgc atcactcaga at                                             22

<210> SEQ ID NO 3
<211> LENGTH: 26
<212> TYPE: DNA
<213> ORGANISM: Artificial Sequence
<220> FEATURE:
<223> OTHER INFORMATION: synthetic salivary transcriptome biomarker
      inner reverse primer ACRV1-IR

<400> SEQUENCE: 3
agttttccac cttcaaagat cttctt                                         26

<210> SEQ ID NO 4
<211> LENGTH: 22
<212> TYPE: DNA
<213> ORGANISM: Artificial Sequence
<220> FEATURE:
<223> OTHER INFORMATION: synthetic salivary transcriptome biomarker
      outer reverse primer ACRV1-OR

<400> SEQUENCE: 4
cacacccttg aaccatgaat tg                                             22

<210> SEQ ID NO 5
<211> LENGTH: 19
<212> TYPE: DNA
<213> ORGANISM: Artificial Sequence
<220> FEATURE:
<223> OTHER INFORMATION: synthetic salivary transcriptome biomarker
      outer forward primer CDC14B-OF

<400> SEQUENCE: 5
ctgcccattg tttggttgc                                                 19

<210> SEQ ID NO 6
<211> LENGTH: 25
<212> TYPE: DNA
<213> ORGANISM: Artificial Sequence
<220> FEATURE:
<223> OTHER INFORMATION: synthetic salivary transcriptome biomarker
      inner forward primer CDC14B-IF

<400> SEQUENCE: 6
gtttggttgc cagtcataca aatta                                          25

<210> SEQ ID NO 7
<211> LENGTH: 20
<212> TYPE: DNA
<213> ORGANISM: Artificial Sequence
<220> FEATURE:
<223> OTHER INFORMATION: synthetic salivary transcriptome biomarker
      inner reverse primer CDC14B-IR

<400> SEQUENCE: 7
attgctgttt ccaaggggaa                                              20

<210> SEQ ID NO 8
<211> LENGTH: 23
<212> TYPE: DNA
<213> ORGANISM: Artificial Sequence
<220> FEATURE:
<223> OTHER INFORMATION: synthetic salivary transcriptome biomarker
      outer reverse primer CDC14B-OR

<400> SEQUENCE: 8
taagccgaca ttatttggga ttg                                          23

<210> SEQ ID NO 9
<211> LENGTH: 25
<212> TYPE: DNA
<213> ORGANISM: Artificial Sequence
<220> FEATURE:
<223> OTHER INFORMATION: synthetic salivary transcriptome biomarker
      outer forward primer ASH2L-OF

<400> SEQUENCE: 9
ctgtctcaaa tgttctccca aagat                                        25

<210> SEQ ID NO 10
<211> LENGTH: 24
<212> TYPE: DNA
<213> ORGANISM: Artificial Sequence
<220> FEATURE:
<223> OTHER INFORMATION: synthetic salivary transcriptome biomarker
      inner forward primer ASH2L-IF

<400> SEQUENCE: 10
caaatgttct cccaaagatg ctaa                                         24

<210> SEQ ID NO 11
<211> LENGTH: 24
<212> TYPE: DNA
<213> ORGANISM: Artificial Sequence
<220> FEATURE:
<223> OTHER INFORMATION: synthetic salivary transcriptome biomarker
      inner reverse primer ASH2L-IR

<400> SEQUENCE: 11
cagtcctacc cagccttta actt                                          24

<210> SEQ ID NO 12
<211> LENGTH: 20
<212> TYPE: DNA
<213> ORGANISM: Artificial Sequence
<220> FEATURE:
<223> OTHER INFORMATION: synthetic salivary transcriptome biomarker
      outer forward primer ASH2L-OF

<400> SEQUENCE: 12
gcagtctccc gcagtcctac                                              20

<210> SEQ ID NO 13
<211> LENGTH: 23
<212> TYPE: DNA
<213> ORGANISM: Artificial Sequence
<220> FEATURE:
<223> OTHER INFORMATION: synthetic salivary transcriptome biomarker outer forward primer STIM2-OF

<400> SEQUENCE: 13
gaaagccacg atggacttac aag                                    23

<210> SEQ ID NO 14
<211> LENGTH: 23
<212> TYPE: DNA
<213> ORGANISM: Artificial Sequence
<220> FEATURE:
<223> OTHER INFORMATION: synthetic salivary transcriptome biomarker inner forward primer STIM2-IF

<400> SEQUENCE: 14
ttaatggact cgtaagccag cat                                    23

<210> SEQ ID NO 15
<211> LENGTH: 27
<212> TYPE: DNA
<213> ORGANISM: Artificial Sequence
<220> FEATURE:
<223> OTHER INFORMATION: synthetic salivary transcriptome biomarker inner reverse primer STIM2-IR

<400> SEQUENCE: 15
agaagatgct ctggtaaaca agaaatt                                27

<210> SEQ ID NO 16
<211> LENGTH: 27
<212> TYPE: DNA
<213> ORGANISM: Artificial Sequence
<220> FEATURE:
<223> OTHER INFORMATION: synthetic salivary transcriptome biomarker outer reverse primer STIM2-OR

<400> SEQUENCE: 16
ctctgtggaa agataagaag atgctct                                27

<210> SEQ ID NO 17
<211> LENGTH: 26
<212> TYPE: DNA
<213> ORGANISM: Artificial Sequence
<220> FEATURE:
<223> OTHER INFORMATION: synthetic salivary transcriptome biomarker outer forward primer GPR124-OF

<400> SEQUENCE: 17
tagaggatct catgacacca tacaca                                 26

<210> SEQ ID NO 18
<211> LENGTH: 20
<212> TYPE: DNA
<213> ORGANISM: Artificial Sequence
<220> FEATURE:
<223> OTHER INFORMATION: synthetic salivary transcriptome biomarker inner forward primer GPR124-IF

<400> SEQUENCE: 18
cccatcattg cctgtgaatg                                        20

```
<210> SEQ ID NO 19
<211> LENGTH: 21
<212> TYPE: DNA
<213> ORGANISM: Artificial Sequence
<220> FEATURE:
<223> OTHER INFORMATION: synthetic salivary transcriptome biomarker
      inner reverse primer GPR124-IR

<400> SEQUENCE: 19
cccagcagta tcaaccctca g                                              21

<210> SEQ ID NO 20
<211> LENGTH: 20
<212> TYPE: DNA
<213> ORGANISM: Artificial Sequence
<220> FEATURE:
<223> OTHER INFORMATION: synthetic salivary transcriptome biomarker
      outer reverse primer GPR124-OR

<400> SEQUENCE: 20
ccctctgctt gtggagtggt                                                20

<210> SEQ ID NO 21
<211> LENGTH: 23
<212> TYPE: DNA
<213> ORGANISM: Artificial Sequence
<220> FEATURE:
<223> OTHER INFORMATION: synthetic salivary transcriptome biomarker
      outer forward primer LILRA2-OF

<400> SEQUENCE: 21
gacagatctg atgatcccag gag                                            23

<210> SEQ ID NO 22
<211> LENGTH: 22
<212> TYPE: DNA
<213> ORGANISM: Artificial Sequence
<220> FEATURE:
<223> OTHER INFORMATION: synthetic salivary transcriptome biomarker
      inner forward primer LILRA2-IF

<400> SEQUENCE: 22
ggctctggag gacaatctag ga                                             22

<210> SEQ ID NO 23
<211> LENGTH: 27
<212> TYPE: DNA
<213> ORGANISM: Artificial Sequence
<220> FEATURE:
<223> OTHER INFORMATION: synthetic salivary transcriptome biomarker
      inner reverse primer LILRA2-IR

<400> SEQUENCE: 23
ctgtctctag aaatgaccag catacag                                        27

<210> SEQ ID NO 24
<211> LENGTH: 25
<212> TYPE: DNA
<213> ORGANISM: Artificial Sequence
<220> FEATURE:
<223> OTHER INFORMATION: synthetic salivary transcriptome biomarker
      outer reverse primer LILRA2-OR

<400> SEQUENCE: 24
tgattgctgt ctctagaaat gacca                                          25

<210> SEQ ID NO 25
```

```
<211> LENGTH: 19
<212> TYPE: DNA
<213> ORGANISM: Artificial Sequence
<220> FEATURE:
<223> OTHER INFORMATION: synthetic salivary transcriptome biomarker
      outer forward primer ENG-OF

<400> SEQUENCE: 25
gcaagaacag tgggcgttg                                              19

<210> SEQ ID NO 26
<211> LENGTH: 20
<212> TYPE: DNA
<213> ORGANISM: Artificial Sequence
<220> FEATURE:
<223> OTHER INFORMATION: synthetic salivary transcriptome biomarker
      inner forward primer ENG-IF

<400> SEQUENCE: 26
gagcctagct cctgccacat                                             20

<210> SEQ ID NO 27
<211> LENGTH: 22
<212> TYPE: DNA
<213> ORGANISM: Artificial Sequence
<220> FEATURE:
<223> OTHER INFORMATION: synthetic salivary transcriptome biomarker
      inner reeverse primer ENG-IR

<400> SEQUENCE: 27
aggacaagca gcttggctac tc                                          22

<210> SEQ ID NO 28
<211> LENGTH: 21
<212> TYPE: DNA
<213> ORGANISM: Artificial Sequence
<220> FEATURE:
<223> OTHER INFORMATION: synthetic salivary transcriptome biomarker
      outer reverse primer ENG-OR

<400> SEQUENCE: 28
caggacaagc agcttggcta c                                           21

<210> SEQ ID NO 29
<211> LENGTH: 26
<212> TYPE: DNA
<213> ORGANISM: Artificial Sequence
<220> FEATURE:
<223> OTHER INFORMATION: synthetic salivary transcriptome biomarker
      outer forward primer RBM24-OF

<400> SEQUENCE: 29
ggttagcatt tttatggact ttctcc                                      26

<210> SEQ ID NO 30
<211> LENGTH: 26
<212> TYPE: DNA
<213> ORGANISM: Artificial Sequence
<220> FEATURE:
<223> OTHER INFORMATION: synthetic salivary transcriptome biomarker
      inner forward primer RBM24-IF

<400> SEQUENCE: 30
ggactttctc cattatcact ggattt                                      26

<210> SEQ ID NO 31
<211> LENGTH: 25
```

```
<212> TYPE: DNA
<213> ORGANISM: Artificial Sequence
<220> FEATURE:
<223> OTHER INFORMATION: synthetic salivary transcriptome biomarker
      inner reverse primer RBM24-IR

<400> SEQUENCE: 31
tgcacaggag agtcatgtct acatt                                          25

<210> SEQ ID NO 32
<211> LENGTH: 28
<212> TYPE: DNA
<213> ORGANISM: Artificial Sequence
<220> FEATURE:
<223> OTHER INFORMATION: synthetic salivary transcriptome biomarker
      outer reverse primer RBM24-OR

<400> SEQUENCE: 32
gaataaataa tttgcacagg agagtcat                                       28

<210> SEQ ID NO 33
<211> LENGTH: 22
<212> TYPE: DNA
<213> ORGANISM: Artificial Sequence
<220> FEATURE:
<223> OTHER INFORMATION: synthetic salivary transcriptome biomarker
      outer forward primer LRRK1-OF

<400> SEQUENCE: 33
gggaaactca atcagcagga ct                                             22

<210> SEQ ID NO 34
<211> LENGTH: 21
<212> TYPE: DNA
<213> ORGANISM: Artificial Sequence
<220> FEATURE:
<223> OTHER INFORMATION: synthetic salivary transcriptome biomarker
      inner forward primer LRRK1-IF

<400> SEQUENCE: 34
caggacttca gaaagggcct t                                              21

<210> SEQ ID NO 35
<211> LENGTH: 20
<212> TYPE: DNA
<213> ORGANISM: Artificial Sequence
<220> FEATURE:
<223> OTHER INFORMATION: synthetic salivary transcriptome biomarker
      inner reverse primer LRRK1-IR

<400> SEQUENCE: 35
ctccagctgc gtccaaattt                                                20

<210> SEQ ID NO 36
<211> LENGTH: 20
<212> TYPE: DNA
<213> ORGANISM: Artificial Sequence
<220> FEATURE:
<223> OTHER INFORMATION: synthetic salivary transcriptome biomarker
      outer reverse primer LRRK1-OR

<400> SEQUENCE: 36
aaacaaacag ggcctgtgct                                                20

<210> SEQ ID NO 37
<211> LENGTH: 26
<212> TYPE: DNA
```

```
<213> ORGANISM: Artificial Sequence
<220> FEATURE:
<223> OTHER INFORMATION: synthetic salivary transcriptome biomarker
      outer forward primer DMXL2-OF

<400> SEQUENCE: 37
gatgtatttc cttggttatg accaaa                                          26

<210> SEQ ID NO 38
<211> LENGTH: 30
<212> TYPE: DNA
<213> ORGANISM: Artificial Sequence
<220> FEATURE:
<223> OTHER INFORMATION: synthetic salivary transcriptome biomarker
      inner forward primer DMXL2-IF

<400> SEQUENCE: 38
gttgagatac tgaaactaat gtctgtgtgt                                      30

<210> SEQ ID NO 39
<211> LENGTH: 28
<212> TYPE: DNA
<213> ORGANISM: Artificial Sequence
<220> FEATURE:
<223> OTHER INFORMATION: synthetic salivary transcriptome biomarker
      inner reverse primer DMXL2-IR

<400> SEQUENCE: 39
ttaacatgat aagacaattt gctggtaa                                        28

<210> SEQ ID NO 40
<211> LENGTH: 24
<212> TYPE: DNA
<213> ORGANISM: Artificial Sequence
<220> FEATURE:
<223> OTHER INFORMATION: synthetic salivary transcriptome biomarker
      outer reverse primer DMXL2-OR

<400> SEQUENCE: 40
acacaggcat tgaacattct catt                                            24

<210> SEQ ID NO 41
<211> LENGTH: 26
<212> TYPE: DNA
<213> ORGANISM: Artificial Sequence
<220> FEATURE:
<223> OTHER INFORMATION: synthetic salivary transcriptome biomarker
      outer forward primer DMD-OF

<400> SEQUENCE: 41
cccaaatgca aacagtctct tctatt                                          26

<210> SEQ ID NO 42
<211> LENGTH: 30
<212> TYPE: DNA
<213> ORGANISM: Artificial Sequence
<220> FEATURE:
<223> OTHER INFORMATION: synthetic salivary transcriptome biomarker
      inner forward primer DMD-IF

<400> SEQUENCE: 42
gcaaacagtc tcttctattt ctttctttt                                       30

<210> SEQ ID NO 43
<211> LENGTH: 23
<212> TYPE: DNA
<213> ORGANISM: Artificial Sequence
```

```
<220> FEATURE:
<223> OTHER INFORMATION: synthetic salivary transcriptome biomarker
      inner reverse primer DMD-IR

<400> SEQUENCE: 43
gtggcaactg gacatcagct tat                                              23

<210> SEQ ID NO 44
<211> LENGTH: 24
<212> TYPE: DNA
<213> ORGANISM: Artificial Sequence
<220> FEATURE:
<223> OTHER INFORMATION: synthetic salivary transcriptome biomarker
      outer reverse primer DMD-OR

<400> SEQUENCE: 44
aattgtcaag tgacgtggga aagt                                             24

<210> SEQ ID NO 45
<211> LENGTH: 24
<212> TYPE: DNA
<213> ORGANISM: Artificial Sequence
<220> FEATURE:
<223> OTHER INFORMATION: synthetic salivary transcriptome biomarker
      outer forward primer MDB3L2-OF

<400> SEQUENCE: 45
gagaaggttc aagtccactg catt                                             24

<210> SEQ ID NO 46
<211> LENGTH: 25
<212> TYPE: DNA
<213> ORGANISM: Artificial Sequence
<220> FEATURE:
<223> OTHER INFORMATION: synthetic salivary transcriptome biomarker
      inner forward primer MDB3L2-IF

<400> SEQUENCE: 46
tgcatttgga gagcgtctta agtat                                            25

<210> SEQ ID NO 47
<211> LENGTH: 20
<212> TYPE: DNA
<213> ORGANISM: Artificial Sequence
<220> FEATURE:
<223> OTHER INFORMATION: synthetic salivary transcriptome biomarker
      inner reverse primer MDB3L2-IR

<400> SEQUENCE: 47
ccagagattc actggccgtc                                                  20

<210> SEQ ID NO 48
<211> LENGTH: 21
<212> TYPE: DNA
<213> ORGANISM: Artificial Sequence
<220> FEATURE:
<223> OTHER INFORMATION: synthetic salivary transcriptome biomarker
      outer reverse primer MDB3L2-OR

<400> SEQUENCE: 48
ctcagcacca gctctgtcca g                                                21

<210> SEQ ID NO 49
<211> LENGTH: 20
<212> TYPE: DNA
<213> ORGANISM: Artificial Sequence
<220> FEATURE:
```

<223> OTHER INFORMATION: synthetic salivary transcriptome biomarker
      outer forward primer ITGA2B-OF

<400> SEQUENCE: 49
cttcccacag cctcctgtca                                                   20

<210> SEQ ID NO 50
<211> LENGTH: 21
<212> TYPE: DNA
<213> ORGANISM: Artificial Sequence
<220> FEATURE:
<223> OTHER INFORMATION: synthetic salivary transcriptome biomarker
      inner forward primer ITGA2B-IF

<400> SEQUENCE: 50
aaccctctca aggtggactg g                                                 21

<210> SEQ ID NO 51
<211> LENGTH: 19
<212> TYPE: DNA
<213> ORGANISM: Artificial Sequence
<220> FEATURE:
<223> OTHER INFORMATION: synthetic salivary transcriptome biomarker
      inner reverse primer ITGA2B-IR

<400> SEQUENCE: 51
ctgcgatccc gcttgtgat                                                    19

<210> SEQ ID NO 52
<211> LENGTH: 22
<212> TYPE: DNA
<213> ORGANISM: Artificial Sequence
<220> FEATURE:
<223> OTHER INFORMATION: synthetic salivary transcriptome biomarker
      outer reverse primer ITGA2B-OR

<400> SEQUENCE: 52
caggaagatc tgtctgcgat cc                                                22

<210> SEQ ID NO 53
<211> LENGTH: 27
<212> TYPE: DNA
<213> ORGANISM: Artificial Sequence
<220> FEATURE:
<223> OTHER INFORMATION: synthetic salivary transcriptome biomarker
      outer forward primer CDH4-OF

<400> SEQUENCE: 53
gatgataatt ctgttctctc caaagca                                           27

<210> SEQ ID NO 54
<211> LENGTH: 25
<212> TYPE: DNA
<213> ORGANISM: Artificial Sequence
<220> FEATURE:
<223> OTHER INFORMATION: synthetic salivary transcriptome biomarker
      inner forward primer CDH4-IF

<400> SEQUENCE: 54
gggtagtctc aatttctgtc agtgc                                             25

<210> SEQ ID NO 55
<211> LENGTH: 26
<212> TYPE: DNA
<213> ORGANISM: Artificial Sequence
<220> FEATURE:
<223> OTHER INFORMATION: synthetic salivary transcriptome biomarker inner reverse primer CDH4-IR

<400> SEQUENCE: 55
gagattctgt gttgattctt ttggtg                                   26

<210> SEQ ID NO 56
<211> LENGTH: 22
<212> TYPE: DNA
<213> ORGANISM: Artificial Sequence
<220> FEATURE:
<223> OTHER INFORMATION: synthetic salivary transcriptome biomarker
      outer reverse primer CDH4-OR

<400> SEQUENCE: 56
ggtcacgtgt gtctgggaga tt                                       22

<210> SEQ ID NO 57
<211> LENGTH: 29
<212> TYPE: DNA
<213> ORGANISM: Artificial Sequence
<220> FEATURE:
<223> OTHER INFORMATION: synthetic salivary transcriptome biomarker
      outer forward primer SAT1-OF

<400> SEQUENCE: 57
cttgaatatc tttcgataaa caacaaggt                                29

<210> SEQ ID NO 58
<211> LENGTH: 28
<212> TYPE: DNA
<213> ORGANISM: Artificial Sequence
<220> FEATURE:
<223> OTHER INFORMATION: synthetic salivary transcriptome biomarker
      inner forward primer SAT1-IF

<400> SEQUENCE: 58
gataaacaac aaggtggtgt gatcttaa                                 28

<210> SEQ ID NO 59
<211> LENGTH: 27
<212> TYPE: DNA
<213> ORGANISM: Artificial Sequence
<220> FEATURE:
<223> OTHER INFORMATION: synthetic salivary transcriptome biomarker
      inner reverse primer SAT1-IR

<400> SEQUENCE: 59
cacatttaaa tgactcacga gaatgaa                                  27

<210> SEQ ID NO 60
<211> LENGTH: 30
<212> TYPE: DNA
<213> ORGANISM: Artificial Sequence
<220> FEATURE:
<223> OTHER INFORMATION: synthetic salivary transcriptome biomarker
      outer reverse primer SAT1-OR

<400> SEQUENCE: 60
caaacagaaa ctctaagtac cagtgtgtac                               30

<210> SEQ ID NO 61
<211> LENGTH: 21
<212> TYPE: DNA
<213> ORGANISM: Artificial Sequence
<220> FEATURE:
<223> OTHER INFORMATION: synthetic salivary transcriptome biomarker
      outer forward primer FTHP1-OF

<400> SEQUENCE: 61
cccatagctg tggggtgact t                                              21

<210> SEQ ID NO 62
<211> LENGTH: 20
<212> TYPE: DNA
<213> ORGANISM: Artificial Sequence
<220> FEATURE:
<223> OTHER INFORMATION: synthetic salivary transcriptome biomarker
      inner forward primer FTHP1-IF

<400> SEQUENCE: 62
caaggcagtg catgcatgtt                                                20

<210> SEQ ID NO 63
<211> LENGTH: 29
<212> TYPE: DNA
<213> ORGANISM: Artificial Sequence
<220> FEATURE:
<223> OTHER INFORMATION: synthetic salivary transcriptome biomarker
      inner reverse primer FTHP1-IR

<400> SEQUENCE: 63
ggtacaaatc aaaagaactt aagtggatg                                      29

<210> SEQ ID NO 64
<211> LENGTH: 27
<212> TYPE: DNA
<213> ORGANISM: Artificial Sequence
<220> FEATURE:
<223> OTHER INFORMATION: synthetic salivary transcriptome biomarker
      outer reverse primer FTHP1-OR

<400> SEQUENCE: 64
tgaaggaatg gtacaaatca aaagaac                                        27

<210> SEQ ID NO 65
<211> LENGTH: 27
<212> TYPE: DNA
<213> ORGANISM: Artificial Sequence
<220> FEATURE:
<223> OTHER INFORMATION: synthetic salivary transcriptome biomarker
      outer forward primer TPT1-OF

<400> SEQUENCE: 65
ggatctatca cctgtcatca taactgg                                        27

<210> SEQ ID NO 66
<211> LENGTH: 25
<212> TYPE: DNA
<213> ORGANISM: Artificial Sequence
<220> FEATURE:
<223> OTHER INFORMATION: synthetic salivary transcriptome biomarker
      outer forward primer ACRV1-OF

<400> SEQUENCE: 66
atcataactg gcttctgctt gtcat                                          25

<210> SEQ ID NO 67
<211> LENGTH: 26
<212> TYPE: DNA
<213> ORGANISM: Artificial Sequence
<220> FEATURE:
<223> OTHER INFORMATION: synthetic salivary transcriptome biomarker
      inner reverse primer TPT1-IR

```
<400> SEQUENCE: 67
gatgacatca gtcccatttg tcttaa                                          26

<210> SEQ ID NO 68
<211> LENGTH: 26
<212> TYPE: DNA
<213> ORGANISM: Artificial Sequence
<220> FEATURE:
<223> OTHER INFORMATION: synthetic salivary transcriptome biomarker
      outer reverse primer TPT1-OR

<400> SEQUENCE: 68
atgaagagct caagatgaca tcagtc                                          26

<210> SEQ ID NO 69
<211> LENGTH: 24
<212> TYPE: DNA
<213> ORGANISM: Artificial Sequence
<220> FEATURE:
<223> OTHER INFORMATION: synthetic salivary transcriptome biomarker
      outer forward primer FTH1-OF

<400> SEQUENCE: 69
cccatttgtg tgacttcatt gaga                                            24

<210> SEQ ID NO 70
<211> LENGTH: 24
<212> TYPE: DNA
<213> ORGANISM: Artificial Sequence
<220> FEATURE:
<223> OTHER INFORMATION: synthetic salivary transcriptome biomarker
      inner forward primer FTH1-IF

<400> SEQUENCE: 70
cattacctga atgagcaggt gaaa                                            24

<210> SEQ ID NO 71
<211> LENGTH: 20
<212> TYPE: DNA
<213> ORGANISM: Artificial Sequence
<220> FEATURE:
<223> OTHER INFORMATION: synthetic salivary transcriptome biomarker
      inner reverse primer FTH1-IR

<400> SEQUENCE: 71
gcaagttggt cacgtggtca                                                 20

<210> SEQ ID NO 72
<211> LENGTH: 19
<212> TYPE: DNA
<213> ORGANISM: Artificial Sequence
<220> FEATURE:
<223> OTHER INFORMATION: synthetic salivary transcriptome biomarker
      outer reverse primer FTH1-OR

<400> SEQUENCE: 72
gctcccatct tgcgcaagt                                                  19

<210> SEQ ID NO 73
<211> LENGTH: 22
<212> TYPE: DNA
<213> ORGANISM: Artificial Sequence
<220> FEATURE:
<223> OTHER INFORMATION: synthetic salivary transcriptome biomarker
      outer forward primer SAT1-OF

<400> SEQUENCE: 73
```
tggcaatctc agatgcagtt tg                                                   22

<210> SEQ ID NO 74
<211> LENGTH: 28
<212> TYPE: DNA
<213> ORGANISM: Artificial Sequence
<220> FEATURE:
<223> OTHER INFORMATION: synthetic salivary transcriptome biomarker
      inner forward primer SAT1-IF

<400> SEQUENCE: 74
ggagagtcag atctttctcc ttgaatat                                              28

<210> SEQ ID NO 75
<211> LENGTH: 28
<212> TYPE: DNA
<213> ORGANISM: Artificial Sequence
<220> FEATURE:
<223> OTHER INFORMATION: synthetic salivary transcriptome biomarker
      inner reverse primer SAT1-IR

<400> SEQUENCE: 75
ttaagatcac accaccttgt tgtttatc                                              28

<210> SEQ ID NO 76
<211> LENGTH: 30
<212> TYPE: DNA
<213> ORGANISM: Artificial Sequence
<220> FEATURE:
<223> OTHER INFORMATION: synthetic salivary transcriptome biomarker
      outer reverse primer SAT1-OR

<400> SEQUENCE: 76
ttcaaatata ttaagatcac accaccttgt                                            30

<210> SEQ ID NO 77
<211> LENGTH: 22
<212> TYPE: DNA
<213> ORGANISM: Artificial Sequence
<220> FEATURE:
<223> OTHER INFORMATION: synthetic salivary transcriptome biomarker
      outer forward primer MARCKS-OF

<400> SEQUENCE: 77
cggcagagta aaagagcaag ct                                                   22

<210> SEQ ID NO 78
<211> LENGTH: 24
<212> TYPE: DNA
<213> ORGANISM: Artificial Sequence
<220> FEATURE:
<223> OTHER INFORMATION: synthetic salivary transcriptome biomarker
      inner forward primer MARCKS-IF

<400> SEQUENCE: 78
gcaagctttt gtgagataat cgaa                                                 24

<210> SEQ ID NO 79
<211> LENGTH: 21
<212> TYPE: DNA
<213> ORGANISM: Artificial Sequence
<220> FEATURE:
<223> OTHER INFORMATION: synthetic salivary transcriptome biomarker
      inner reverse primer MARCKS-IR

<400> SEQUENCE: 79
ggcaccactc aacaaacaa a                                              21

<210> SEQ ID NO 80
<211> LENGTH: 24
<212> TYPE: DNA
<213> ORGANISM: Artificial Sequence
<220> FEATURE:
<223> OTHER INFORMATION: synthetic salivary transcriptome biomarker
      outer reverse primer MARCKS-OR

<400> SEQUENCE: 80
cctggttgta gacaagttct ccaa                                          24

<210> SEQ ID NO 81
<211> LENGTH: 19
<212> TYPE: DNA
<213> ORGANISM: Artificial Sequence
<220> FEATURE:
<223> OTHER INFORMATION: synthetic salivary transcriptome biomarker
      outer forward primer PNPLA8-OF

<400> SEQUENCE: 81
tggccagatg tgccgttag                                                19

<210> SEQ ID NO 82
<211> LENGTH: 26
<212> TYPE: DNA
<213> ORGANISM: Artificial Sequence
<220> FEATURE:
<223> OTHER INFORMATION: synthetic salivary transcriptome biomarker
      inner forward primer PNPLA8-IF

<400> SEQUENCE: 82
agatgtgccg ttagagtgca tagtat                                        26

<210> SEQ ID NO 83
<211> LENGTH: 24
<212> TYPE: DNA
<213> ORGANISM: Artificial Sequence
<220> FEATURE:
<223> OTHER INFORMATION: synthetic salivary transcriptome biomarker
      inner reverse primer PNPLA8-IR

<400> SEQUENCE: 83
ccgtgtttct cacatcactc tcat                                          24

<210> SEQ ID NO 84
<211> LENGTH: 25
<212> TYPE: DNA
<213> ORGANISM: Artificial Sequence
<220> FEATURE:
<223> OTHER INFORMATION: synthetic salivary transcriptome biomarker
      outer reverse primer PNPLA8-OR

<400> SEQUENCE: 84
tcaagcttgt gtatgttacc gtgtt                                         25

<210> SEQ ID NO 85
<211> LENGTH: 21
<212> TYPE: DNA
<213> ORGANISM: Artificial Sequence
<220> FEATURE:
<223> OTHER INFORMATION: synthetic salivary transcriptome biomarker
      outer forward primer DPM1-OF

<400> SEQUENCE: 85
gagatgattg ttcgggcaag a                                             21

<210> SEQ ID NO 86
<211> LENGTH: 24
<212> TYPE: DNA
<213> ORGANISM: Artificial Sequence
<220> FEATURE:
<223> OTHER INFORMATION: synthetic salivary transcriptome biomarker
      inner forward primer DPM1-IF

<400> SEQUENCE: 86
ttcgggcaag acagttgaat tata                                         24

<210> SEQ ID NO 87
<211> LENGTH: 23
<212> TYPE: DNA
<213> ORGANISM: Artificial Sequence
<220> FEATURE:
<223> OTHER INFORMATION: synthetic salivary transcriptome biomarker
      inner reverse primer DPM1-IR

<400> SEQUENCE: 87
tcaccataaa cacgatccac aaa                                          23

<210> SEQ ID NO 88
<211> LENGTH: 22
<212> TYPE: DNA
<213> ORGANISM: Artificial Sequence
<220> FEATURE:
<223> OTHER INFORMATION: synthetic salivary transcriptome biomarker
      outer reverse primer DPM1-OR

<400> SEQUENCE: 88
ttcatttcct cccaacttgg at                                           22

<210> SEQ ID NO 89
<211> LENGTH: 19
<212> TYPE: DNA
<213> ORGANISM: Artificial Sequence
<220> FEATURE:
<223> OTHER INFORMATION: synthetic salivary transcriptome biomarker
      outer forward primer CD7-OF

<400> SEQUENCE: 89
tggcggtgat ctccttcct                                               19

<210> SEQ ID NO 90
<211> LENGTH: 21
<212> TYPE: DNA
<213> ORGANISM: Artificial Sequence
<220> FEATURE:
<223> OTHER INFORMATION: synthetic salivary transcriptome biomarker
      inner forward primer CD7-IF

<400> SEQUENCE: 90
gctggcgagg acacagataa a                                            21

<210> SEQ ID NO 91
<211> LENGTH: 20
<212> TYPE: DNA
<213> ORGANISM: Artificial Sequence
<220> FEATURE:
<223> OTHER INFORMATION: synthetic salivary transcriptome biomarker
      inner reverse primer CD7-IR

<400> SEQUENCE: 91
atgccgccga attcttatcc                                              20

<210> SEQ ID NO 92
<211> LENGTH: 21
<212> TYPE: DNA
<213> ORGANISM: Artificial Sequence
<220> FEATURE:
<223> OTHER INFORMATION: synthetic salivary transcriptome biomarker outer reverse primer CD7-OR

<400> SEQUENCE: 92
tgtgcgacat gtcctcgtac a                                              21

<210> SEQ ID NO 93
<211> LENGTH: 21
<212> TYPE: DNA
<213> ORGANISM: Artificial Sequence
<220> FEATURE:
<223> OTHER INFORMATION: synthetic salivary transcriptome biomarker outer forward primer GPR37-OF

<400> SEQUENCE: 93
gaagtggctg ctggaggact t                                              21

<210> SEQ ID NO 94
<211> LENGTH: 21
<212> TYPE: DNA
<213> ORGANISM: Artificial Sequence
<220> FEATURE:
<223> OTHER INFORMATION: synthetic salivary transcriptome biomarker inner forward primer GPR37-IF

<400> SEQUENCE: 94
cctgcaagat cgtgccctat a                                              21

<210> SEQ ID NO 95
<211> LENGTH: 22
<212> TYPE: DNA
<213> ORGANISM: Artificial Sequence
<220> FEATURE:
<223> OTHER INFORMATION: synthetic salivary transcriptome biomarker inner reverse primer GPR37-IR

<400> SEQUENCE: 95
tgcacagagc acataaggtg aa                                             22

<210> SEQ ID NO 96
<211> LENGTH: 19
<212> TYPE: DNA
<213> ORGANISM: Artificial Sequence
<220> FEATURE:
<223> OTHER INFORMATION: synthetic salivary transcriptome biomarker outer reverse primer ACRV1-OR

<400> SEQUENCE: 96
cacggaagcg gtctatgca                                                 19

<210> SEQ ID NO 97
<211> LENGTH: 20
<212> TYPE: DNA
<213> ORGANISM: Artificial Sequence
<220> FEATURE:
<223> OTHER INFORMATION: synthetic salivary transcriptome biomarker outer forward primer PCSK6-OF

<400> SEQUENCE: 97
acctcctgca tcaccaacca                                                20

```
<210> SEQ ID NO 98
<211> LENGTH: 21
<212> TYPE: DNA
<213> ORGANISM: Artificial Sequence
<220> FEATURE:
<223> OTHER INFORMATION: synthetic salivary transcriptome biomarker
      inner forward primer PCSK6-IF

<400> SEQUENCE: 98
agcaacgctg acgagacatt c                                               21

<210> SEQ ID NO 99
<211> LENGTH: 19
<212> TYPE: DNA
<213> ORGANISM: Artificial Sequence
<220> FEATURE:
<223> OTHER INFORMATION: synthetic salivary transcriptome biomarker
      inner reverse primer PCSK6-IR

<400> SEQUENCE: 99
cacagccggt tggacttca                                                  19

<210> SEQ ID NO 100
<211> LENGTH: 20
<212> TYPE: DNA
<213> ORGANISM: Artificial Sequence
<220> FEATURE:
<223> OTHER INFORMATION: synthetic salivary transcriptome biomarker
      outer reverse primer PCSK6-OR

<400> SEQUENCE: 100
cggcagcaga actgaatgaa                                                 20

<210> SEQ ID NO 101
<211> LENGTH: 20
<212> TYPE: DNA
<213> ORGANISM: Artificial Sequence
<220> FEATURE:
<223> OTHER INFORMATION: synthetic salivary transcriptome biomarker
      outer forward primer TK2-OF

<400> SEQUENCE: 101
gcccctgttc tggtgattga                                                 20

<210> SEQ ID NO 102
<211> LENGTH: 22
<212> TYPE: DNA
<213> ORGANISM: Artificial Sequence
<220> FEATURE:
<223> OTHER INFORMATION: synthetic salivary transcriptome biomarker
      inner forward primer TK2-IF

<400> SEQUENCE: 102
ccaccacatg gagaggatgt ta                                              22

<210> SEQ ID NO 103
<211> LENGTH: 25
<212> TYPE: DNA
<213> ORGANISM: Artificial Sequence
<220> FEATURE:
<223> OTHER INFORMATION: synthetic salivary transcriptome biomarker
      inner reverse primer TK2-IR

<400> SEQUENCE: 103
tccgattctc tggagttaat attcg                                           25

<210> SEQ ID NO 104
```

-continued

```
<211> LENGTH: 23
<212> TYPE: DNA
<213> ORGANISM: Artificial Sequence
<220> FEATURE:
<223> OTHER INFORMATION: synthetic salivary transcriptome biomarker
      outer reverse primer TK2-OR

<400> SEQUENCE: 104
agccatagac cttttgcctc cta                                              23

<210> SEQ ID NO 105
<211> LENGTH: 24
<212> TYPE: DNA
<213> ORGANISM: Artificial Sequence
<220> FEATURE:
<223> OTHER INFORMATION: synthetic salivary transcriptome biomarker
      outer forward primer TTBK2-OF

<400> SEQUENCE: 105
tagaagccag gctacgcaga tata                                             24

<210> SEQ ID NO 106
<211> LENGTH: 20
<212> TYPE: DNA
<213> ORGANISM: Artificial Sequence
<220> FEATURE:
<223> OTHER INFORMATION: synthetic salivary transcriptome biomarker
      inner forward primer TTBK2-IF

<400> SEQUENCE: 106
cctggcccaa attcttcaaa                                                  20

<210> SEQ ID NO 107
<211> LENGTH: 24
<212> TYPE: DNA
<213> ORGANISM: Artificial Sequence
<220> FEATURE:
<223> OTHER INFORMATION: synthetic salivary transcriptome biomarker
      inner reverse primer TTBK2-IR

<400> SEQUENCE: 107
cctggactct tgcactgagt agtg                                             24

<210> SEQ ID NO 108
<211> LENGTH: 24
<212> TYPE: DNA
<213> ORGANISM: Artificial Sequence
<220> FEATURE:
<223> OTHER INFORMATION: synthetic salivary transcriptome biomarker
      outer reverse primer TTBK2-OR

<400> SEQUENCE: 108
agatcctgga ctcttgcact gagt                                             24

<210> SEQ ID NO 109
<211> LENGTH: 20
<212> TYPE: DNA
<213> ORGANISM: Artificial Sequence
<220> FEATURE:
<223> OTHER INFORMATION: synthetic salivary transcriptome biomarker
      outer forward primer GLTSCR2-OF

<400> SEQUENCE: 109
gaccggttca agagcttcca                                                  20

<210> SEQ ID NO 110
<211> LENGTH: 23
```

<212> TYPE: DNA
<213> ORGANISM: Artificial Sequence
<220> FEATURE:
<223> OTHER INFORMATION: synthetic salivary transcriptome biomarker
      inner forward primer GLTSCR2-IF

<400> SEQUENCE: 110
ttccagagga ggaatatgat cga                                      23

<210> SEQ ID NO 111
<211> LENGTH: 23
<212> TYPE: DNA
<213> ORGANISM: Artificial Sequence
<220> FEATURE:
<223> OTHER INFORMATION: synthetic salivary transcriptome biomarker
      inner reverse primer GLTSCR2-IR

<400> SEQUENCE: 111
ttctccacca gcttcacctt gta                                      23

<210> SEQ ID NO 112
<211> LENGTH: 23
<212> TYPE: DNA
<213> ORGANISM: Artificial Sequence
<220> FEATURE:
<223> OTHER INFORMATION: synthetic salivary transcriptome biomarker
      outer reverse primer GLTSCR2-OR

<400> SEQUENCE: 112
tgatggcagc tacaactgga tct                                      23

<210> SEQ ID NO 113
<211> LENGTH: 25
<212> TYPE: DNA
<213> ORGANISM: Artificial Sequence
<220> FEATURE:
<223> OTHER INFORMATION: synthetic salivary transcriptome biomarker
      outer forward primer CDKL3-OF

<400> SEQUENCE: 113
tcagttttgg gagaggaaat agaaa                                    25

<210> SEQ ID NO 114
<211> LENGTH: 25
<212> TYPE: DNA
<213> ORGANISM: Artificial Sequence
<220> FEATURE:
<223> OTHER INFORMATION: synthetic salivary transcriptome biomarker
      inner forward primer CDKL3-IF

<400> SEQUENCE: 114
tagaaaaaga gaaaaagccc aagga                                    25

<210> SEQ ID NO 115
<211> LENGTH: 26
<212> TYPE: DNA
<213> ORGANISM: Artificial Sequence
<220> FEATURE:
<223> OTHER INFORMATION: synthetic salivary transcriptome biomarker
      inner reverse primer CDKL3-IR

<400> SEQUENCE: 115
tctcctcttc ctcctttgac tttaat                                   26

<210> SEQ ID NO 116
<211> LENGTH: 26
<212> TYPE: DNA

```
<213> ORGANISM: Artificial Sequence
<220> FEATURE:
<223> OTHER INFORMATION: synthetic salivary transcriptome biomarker
      outer reverse primer CDKL3-OR

<400> SEQUENCE: 116
tccaccttca tactctttct tttttg                                          26

<210> SEQ ID NO 117
<211> LENGTH: 23
<212> TYPE: DNA
<213> ORGANISM: Artificial Sequence
<220> FEATURE:
<223> OTHER INFORMATION: synthetic salivary transcriptome biomarker
      outer forward primer ZSCAN16-OF

<400> SEQUENCE: 117
ctcctcagca tcctaagtcc aaa                                             23

<210> SEQ ID NO 118
<211> LENGTH: 19
<212> TYPE: DNA
<213> ORGANISM: Artificial Sequence
<220> FEATURE:
<223> OTHER INFORMATION: synthetic salivary transcriptome biomarker
      inner forward primer ZSCAN16-IF

<400> SEQUENCE: 118
gggcagatca gaatggcaa                                                  19

<210> SEQ ID NO 119
<211> LENGTH: 27
<212> TYPE: DNA
<213> ORGANISM: Artificial Sequence
<220> FEATURE:
<223> OTHER INFORMATION: synthetic salivary transcriptome biomarker
      inner reverse primer ZSCAN16-IR

<400> SEQUENCE: 119
ccacattcat cacatttata tcgtctt                                         27

<210> SEQ ID NO 120
<211> LENGTH: 25
<212> TYPE: DNA
<213> ORGANISM: Artificial Sequence
<220> FEATURE:
<223> OTHER INFORMATION: synthetic salivary transcriptome biomarker
      outer reverse primer ZSCAN16-OR

<400> SEQUENCE: 120
gctatgactg aaacttttcc cacat                                           25

<210> SEQ ID NO 121
<211> LENGTH: 18
<212> TYPE: DNA
<213> ORGANISM: Artificial Sequence
<220> FEATURE:
<223> OTHER INFORMATION: synthetic salivary transcriptome biomarker
      outer forward primer S100P-OF

<400> SEQUENCE: 121
gcacgcagac cctgacca                                                   18

<210> SEQ ID NO 122
<211> LENGTH: 22
<212> TYPE: DNA
<213> ORGANISM: Artificial Sequence
```

```
<220> FEATURE:
<223> OTHER INFORMATION: synthetic salivary transcriptome biomarker
      inner forward primer S100P-IF

<400> SEQUENCE: 122
gctgatggag aaggagctac ca                                              22

<210> SEQ ID NO 123
<211> LENGTH: 22
<212> TYPE: DNA
<213> ORGANISM: Artificial Sequence
<220> FEATURE:
<223> OTHER INFORMATION: synthetic salivary transcriptome biomarker
      inner reverse primer S100P-IR

<400> SEQUENCE: 123
ttgagcaatt tatccacggc at                                              22

<210> SEQ ID NO 124
<211> LENGTH: 21
<212> TYPE: DNA
<213> ORGANISM: Artificial Sequence
<220> FEATURE:
<223> OTHER INFORMATION: synthetic salivary transcriptome biomarker
      outer reverse primer S100P-OR

<400> SEQUENCE: 124
cgtccaggtc cttgagcaat t                                               21

<210> SEQ ID NO 125
<211> LENGTH: 24
<212> TYPE: DNA
<213> ORGANISM: Artificial Sequence
<220> FEATURE:
<223> OTHER INFORMATION: synthetic salivary transcriptome biomarker
      outer forward primer KRAS-OF

<400> SEQUENCE: 125
agacacaaaa caggctcagg actt                                            24

<210> SEQ ID NO 126
<211> LENGTH: 23
<212> TYPE: DNA
<213> ORGANISM: Artificial Sequence
<220> FEATURE:
<223> OTHER INFORMATION: synthetic salivary transcriptome biomarker
      inner forward primer KRAS-IF

<400> SEQUENCE: 126
caggctcagg acttagcaag aag                                             23

<210> SEQ ID NO 127
<211> LENGTH: 23
<212> TYPE: DNA
<213> ORGANISM: Artificial Sequence
<220> FEATURE:
<223> OTHER INFORMATION: synthetic salivary transcriptome biomarker
      inner reverse primer KRAS-IR

<400> SEQUENCE: 127
caccctgtct tgtctttgct gat                                             23

<210> SEQ ID NO 128
<211> LENGTH: 21
<212> TYPE: DNA
<213> ORGANISM: Artificial Sequence
<220> FEATURE:
```

-continued

```
<223> OTHER INFORMATION: synthetic salivary transcriptome biomarker
      outer reverse primer KRAS-OR

<400> SEQUENCE: 128
ggcatcatca acaccctgtc t                                              21

<210> SEQ ID NO 129
<211> LENGTH: 17
<212> TYPE: DNA
<213> ORGANISM: Artificial Sequence
<220> FEATURE:
<223> OTHER INFORMATION: synthetic salivary transcriptome biomarker
      outer forward primer UTF1-OF

<400> SEQUENCE: 129
cccccgtcgc tgaacac                                                   17

<210> SEQ ID NO 130
<211> LENGTH: 18
<212> TYPE: DNA
<213> ORGANISM: Artificial Sequence
<220> FEATURE:
<223> OTHER INFORMATION: synthetic salivary transcriptome biomarker
      inner forward primer UTF1-IF

<400> SEQUENCE: 130
ggcgacatcg cgaacatc                                                  18

<210> SEQ ID NO 131
<211> LENGTH: 19
<212> TYPE: DNA
<213> ORGANISM: Artificial Sequence
<220> FEATURE:
<223> OTHER INFORMATION: synthetic salivary transcriptome biomarker
      inner reverse primer UTF1-IR

<400> SEQUENCE: 131
gctccacgtg ctggttcaa                                                 19

<210> SEQ ID NO 132
<211> LENGTH: 18
<212> TYPE: DNA
<213> ORGANISM: Artificial Sequence
<220> FEATURE:
<223> OTHER INFORMATION: synthetic salivary transcriptome biomarker
      outer reverse primer UTF1-OR

<400> SEQUENCE: 132
cggccaggga cactgtct                                                  18

<210> SEQ ID NO 133
<211> LENGTH: 18
<212> TYPE: DNA
<213> ORGANISM: Artificial Sequence
<220> FEATURE:
<223> OTHER INFORMATION: synthetic salivary transcriptome biomarker
      outer forward primer ZMIZ2-OF

<400> SEQUENCE: 133
ggacctgctc ccggaact                                                  18

<210> SEQ ID NO 134
<211> LENGTH: 22
<212> TYPE: DNA
<213> ORGANISM: Artificial Sequence
<220> FEATURE:
<223> OTHER INFORMATION: synthetic salivary transcriptome biomarker
``` inner forward primer ZMIZ2-IF

<400> SEQUENCE: 134
ggaactgacc aaccctgatg ag                                            22

<210> SEQ ID NO 135
<211> LENGTH: 23
<212> TYPE: DNA
<213> ORGANISM: Artificial Sequence
<220> FEATURE:
<223> OTHER INFORMATION: synthetic salivary transcriptome biomarker
      inner reverse primer ZMIZ2-IR

<400> SEQUENCE: 135
caggtcgtca ttgttgttcg tag                                           23

<210> SEQ ID NO 136
<211> LENGTH: 23
<212> TYPE: DNA
<213> ORGANISM: Artificial Sequence
<220> FEATURE:
<223> OTHER INFORMATION: synthetic salivary transcriptome biomarker
      outer reverse primer ZMIZ2-OR

<400> SEQUENCE: 136
aacagagaaa gcaggtcgtc att                                           23

<210> SEQ ID NO 137
<211> LENGTH: 22
<212> TYPE: DNA
<213> ORGANISM: Artificial Sequence
<220> FEATURE:
<223> OTHER INFORMATION: synthetic salivary transcriptome biomarker
      outer forward primer DDX3X-OF

<400> SEQUENCE: 137
gaggtggcta tggaggcttt ta                                            22

<210> SEQ ID NO 138
<211> LENGTH: 24
<212> TYPE: DNA
<213> ORGANISM: Artificial Sequence
<220> FEATURE:
<223> OTHER INFORMATION: synthetic salivary transcriptome biomarker
      inner forward primer DDX3X-IF

<400> SEQUENCE: 138
caacagtgat ggatatggag gaaa                                          24

<210> SEQ ID NO 139
<211> LENGTH: 22
<212> TYPE: DNA
<213> ORGANISM: Artificial Sequence
<220> FEATURE:
<223> OTHER INFORMATION: synthetic salivary transcriptome biomarker
      inner reverse primer DDX3X-IR

<400> SEQUENCE: 139
gctcagttac cccaccagtc aa                                            22

<210> SEQ ID NO 140
<211> LENGTH: 21
<212> TYPE: DNA
<213> ORGANISM: Artificial Sequence
<220> FEATURE:
<223> OTHER INFORMATION: synthetic salivary transcriptome biomarker
      outer reverse primer DDX3X-OR

<400> SEQUENCE: 140
tgtttggcag ggtgacctac t                                              21

<210> SEQ ID NO 141
<211> LENGTH: 21
<212> TYPE: DNA
<213> ORGANISM: Artificial Sequence
<220> FEATURE:
<223> OTHER INFORMATION: synthetic salivary transcriptome biomarker
      outer forward primer CABLES1-OF

<400> SEQUENCE: 141
gtcctcagcc ttgtggtagc a                                              21

<210> SEQ ID NO 142
<211> LENGTH: 24
<212> TYPE: DNA
<213> ORGANISM: Artificial Sequence
<220> FEATURE:
<223> OTHER INFORMATION: synthetic salivary transcriptome biomarker
      inner forward primer CABLES1-IF

<400> SEQUENCE: 142
tggtagcaca aatgaatgca gtaa                                           24

<210> SEQ ID NO 143
<211> LENGTH: 23
<212> TYPE: DNA
<213> ORGANISM: Artificial Sequence
<220> FEATURE:
<223> OTHER INFORMATION: synthetic salivary transcriptome biomarker
      inner reverse primer CABLES1-IR

<400> SEQUENCE: 143
gcagtattct gtgaacgctg gta                                            23

<210> SEQ ID NO 144
<211> LENGTH: 26
<212> TYPE: DNA
<213> ORGANISM: Artificial Sequence
<220> FEATURE:
<223> OTHER INFORMATION: synthetic salivary transcriptome biomarker
      outer reverse primer CABLES1-OR

<400> SEQUENCE: 144
caagatttga ggttcagtgc agtatt                                         26

<210> SEQ ID NO 145
<211> LENGTH: 21
<212> TYPE: DNA
<213> ORGANISM: Artificial Sequence
<220> FEATURE:
<223> OTHER INFORMATION: synthetic outer forward primer GAPDH-OF

<400> SEQUENCE: 145
cattgccctc aacgaccact t                                              21

<210> SEQ ID NO 146
<211> LENGTH: 24
<212> TYPE: DNA
<213> ORGANISM: Artificial Sequence
<220> FEATURE:
<223> OTHER INFORMATION: synthetic inner forward primer GAPDH-IF

<400> SEQUENCE: 146
accactttgt caagctcatt tcct                                      24

<210> SEQ ID NO 147
<211> LENGTH: 22
<212> TYPE: DNA
<213> ORGANISM: Artificial Sequence
<220> FEATURE:
<223> OTHER INFORMATION: synthetic salivary transcriptome biomarker
      inner reverse primer GAPDH-IR

<400> SEQUENCE: 147
caccctgttg ctgtagccaa at                                        22

<210> SEQ ID NO 148
<211> LENGTH: 19
<212> TYPE: DNA
<213> ORGANISM: Artificial Sequence
<220> FEATURE:
<223> OTHER INFORMATION: synthetic salivary transcriptome biomarker
      outer reverse primer GAPDH-OR

<400> SEQUENCE: 148
atgtgggcca tgaggtcca                                            19

<210> SEQ ID NO 149
<211> LENGTH: 22
<212> TYPE: DNA
<213> ORGANISM: Artificial Sequence
<220> FEATURE:
<223> OTHER INFORMATION: synthetic microbial biomarker Atopobium
      parvulum 16S rRNA primer F

<400> SEQUENCE: 149
cgaatacttc gagacttccg ca                                        22

<210> SEQ ID NO 150
<211> LENGTH: 20
<212> TYPE: DNA
<213> ORGANISM: Artificial Sequence
<220> FEATURE:
<223> OTHER INFORMATION: synthetic microbial biomarker Atopobium
      parvulum 16S rRNA primer R

<400> SEQUENCE: 150
caatctggct ggtcggtctc                                           20

<210> SEQ ID NO 151
<211> LENGTH: 22
<212> TYPE: DNA
<213> ORGANISM: Artificial Sequence
<220> FEATURE:
<223> OTHER INFORMATION: synthetic microbial biomarker Granulicatella
      adiacens 16S rRNA primer F

<400> SEQUENCE: 151
caagcttctg ctgatggatg ga                                        22

<210> SEQ ID NO 152
<211> LENGTH: 21
<212> TYPE: DNA
<213> ORGANISM: Artificial Sequence
<220> FEATURE:
<223> OTHER INFORMATION: synthetic microbial biomarker Granulicatella
      adiacens 16S rRNA primer R

<400> SEQUENCE: 152
ctcaggtcgg ctatgcatca c                                         21

<210> SEQ ID NO 153
<211> LENGTH: 20
<212> TYPE: DNA
<213> ORGANISM: Artificial Sequence
<220> FEATURE:
<223> OTHER INFORMATION: synthetic microbial biomarker Neisseria
    elongata 16S rRNA primer F

<400> SEQUENCE: 153
catgccgcgt gtctgaagaa                    20

<210> SEQ ID NO 154
<211> LENGTH: 21
<212> TYPE: DNA
<213> ORGANISM: Artificial Sequence
<220> FEATURE:
<223> OTHER INFORMATION: synthetic microbial biomarker Neisseria
    elongata 16S rRNA primer R

<400> SEQUENCE: 154
ccgtcagcag aaacgggtat t                  21

<210> SEQ ID NO 155
<211> LENGTH: 21
<212> TYPE: DNA
<213> ORGANISM: Artificial Sequence
<220> FEATURE:
<223> OTHER INFORMATION: synthetic microbial biomarker Prevotella
    nigrescens 16S rRNA primer F

<400> SEQUENCE: 155
gacggcatcc gatatgaaac a                  21

<210> SEQ ID NO 156
<211> LENGTH: 19
<212> TYPE: DNA
<213> ORGANISM: Artificial Sequence
<220> FEATURE:
<223> OTHER INFORMATION: synthetic microbial biomarker Prevotella
    nigrescens 16S rRNA primer R

<400> SEQUENCE: 156
tgcacgctac ttggctggt                     19

<210> SEQ ID NO 157
<211> LENGTH: 22
<212> TYPE: DNA
<213> ORGANISM: Artificial Sequence
<220> FEATURE:
<223> OTHER INFORMATION: synthetic microbial biomarker Streptococcus
    australis 16S rRNA primer F

<400> SEQUENCE: 157
agaacgctga aggaaggagc tt                 22

<210> SEQ ID NO 158
<211> LENGTH: 22
<212> TYPE: DNA
<213> ORGANISM: Artificial Sequence
<220> FEATURE:
<223> OTHER INFORMATION: synthetic microbial biomarker Streptococcus
    australis 16S rRNA primer R

<400> SEQUENCE: 158
caatagttat cccccgctac ca                 22

```
<210> SEQ ID NO 159
<211> LENGTH: 22
<212> TYPE: DNA
<213> ORGANISM: Artificial Sequence
<220> FEATURE:
<223> OTHER INFORMATION: synthetic microbial biomarker Streptococcus
      mitis 16S rRNA primer F

<400> SEQUENCE: 159
ccgcataata gcagttrttg ca                                              22

<210> SEQ ID NO 160
<211> LENGTH: 21
<212> TYPE: DNA
<213> ORGANISM: Artificial Sequence
<220> FEATURE:
<223> OTHER INFORMATION: synthetic microbial biomarker Streptococcus
      mitis 16S rRNA primer R

<400> SEQUENCE: 160
acaacgcagg tccatctggt a                                               21

<210> SEQ ID NO 161
<211> LENGTH: 4
<212> TYPE: PRT
<213> ORGANISM: Artificial Sequence
<220> FEATURE:
<223> OTHER INFORMATION: synthetic DEAD box

<400> SEQUENCE: 161

Asp Glu Ala Asp
```